(12) United States Patent
Shelley et al.

(10) Patent No.: US 8,251,912 B2
(45) Date of Patent: Aug. 28, 2012

(54) METHOD OF ASSESSING BLOOD VOLUME USING PHOTOELECTRIC PLETHYSMOGRAPHY

(75) Inventors: Kirk H. Shelley, New Haven, CT (US); David G. Silverman, West Redding, CT (US); Adam J. Shelley, New Haven, CT (US); Robert G. Stout, Madison, CT (US)

(73) Assignee: Yale University, New Haven, CT (US)

( * ) Notice: Subject to any disclaimer, the term of this patent is extended or adjusted under 35 U.S.C. 154(b) by 1746 days.

(21) Appl. No.: 10/548,518

(22) PCT Filed: Jan. 2, 2004

(86) PCT No.: PCT/US2004/000027
§ 371 (c)(1),
(2), (4) Date: Jun. 19, 2006

(87) PCT Pub. No.: WO2004/080300
PCT Pub. Date: Sep. 23, 2004

(65) Prior Publication Data
US 2007/0032732 A1    Feb. 8, 2007

Related U.S. Application Data

(60) Provisional application No. 60/465,609, filed on Apr. 25, 2003, provisional application No. 60/454,048, filed on Mar. 12, 2003.

(51) Int. Cl.
*A61B 5/08* (2006.01)
*A61B 5/02* (2006.01)
(52) U.S. Cl. .................. 600/484; 600/504; 600/483
(58) Field of Classification Search .......... 600/529–543, 600/595, 587, 481, 483–485, 500–507
See application file for complete search history.

(56) References Cited

U.S. PATENT DOCUMENTS

| 4,800,495 A | 1/1989 | Smith |
| 4,860,759 A | 8/1989 | Kahn et al. |

(Continued)

FOREIGN PATENT DOCUMENTS

DE    196 50 738    6/1998

(Continued)

OTHER PUBLICATIONS

Supplementary European Search Report dated Jun. 16, 2009.

(Continued)

*Primary Examiner* — Navin Natnithithadha
(74) *Attorney, Agent, or Firm* — McCarter & English, LLP

(57) ABSTRACT

A method and system for assessing blood volume within a subject includes generating a cardiovascular waveform representing physiological characteristics of a subject and determining blood volume of the subject by analyzing the cardiovascular waveform. The step of analyzing includes generating a first trace of the per heart-beat maximums of the cardiovascular waveform, which is representative of the systolic pressure upon the cardiovascular signal, generating a second trace of the per heart-beat minimums of the cardiovascular waveform, which is representative of the diastolic pressure upon the cardiovascular signal, and comparing the respective first trace and the second trace to generate an estimate of relative blood volume within the subject. In accordance with an alternate method of analyzing harmonic analysis is applied to the cardiovascular waveform, extracting a frequency signal created by ventilation and applying the extracted frequency signal in determining blood volume of the subject.

62 Claims, 16 Drawing Sheets

U.S. PATENT DOCUMENTS

| | | | |
|---|---|---|---|
| 5,396,893 A | 3/1995 | Oberg et al. | |
| 5,482,036 A | 1/1996 | Diab et al. | |
| 5,490,505 A | 2/1996 | Diab et al. | |
| 5,769,082 A | 6/1998 | Perel | |
| 5,865,756 A | 2/1999 | Peel, III | |
| 6,002,952 A | 12/1999 | Diab et al. | |
| 6,036,642 A | 3/2000 | Diab et al. | |
| 6,067,462 A | 5/2000 | Diab et al. | |
| 6,081,742 A * | 6/2000 | Amano et al. | 600/513 |
| 6,129,675 A | 10/2000 | Jay | |
| 6,206,830 B1 | 3/2001 | Diab et al. | |
| 6,319,205 B1 | 11/2001 | Goor et al. | |
| 6,322,515 B1 | 11/2001 | Goor et al. | |
| 6,325,761 B1 | 12/2001 | Jay | |
| 6,334,065 B1 | 12/2001 | Al-Ali et al. | |
| 6,361,501 B1 * | 3/2002 | Amano et al. | 600/500 |
| 6,463,311 B1 | 10/2002 | Diab | |
| 6,480,729 B2 | 11/2002 | Stone | |
| 6,501,975 B2 | 12/2002 | Diab et al. | |
| 6,506,161 B2 | 1/2003 | Brockway et al. | |
| 6,561,984 B1 | 5/2003 | Turcott | |
| 6,616,613 B1 * | 9/2003 | Goodman | 600/504 |
| 6,658,277 B2 | 12/2003 | Wasserman | |
| 6,669,632 B2 * | 12/2003 | Nanba et al. | 600/300 |
| 6,699,194 B1 | 3/2004 | Diab et al. | |
| 6,702,752 B2 * | 3/2004 | Dekker | 600/484 |
| 6,709,402 B2 | 3/2004 | Dekker | |
| 6,714,804 B2 | 3/2004 | Al-Ali et al. | |
| 6,826,419 B2 | 11/2004 | Diab et al. | |
| 6,869,402 B2 | 3/2005 | Arnold | |
| 6,896,661 B2 * | 5/2005 | Dekker | 600/529 |
| 6,898,452 B2 | 5/2005 | Al-Ali et al. | |
| 7,001,337 B2 | 2/2006 | Dekker | |
| 7,027,850 B2 | 4/2006 | Wasserman | |
| 7,209,775 B2 | 4/2007 | Bae et al. | |
| 7,471,971 B2 | 12/2008 | Diab et al. | |
| 7,489,958 B2 | 2/2009 | Diab et al. | |
| 7,499,741 B2 | 3/2009 | Diab et al. | |
| 7,515,949 B2 | 4/2009 | Norris | |
| 7,976,472 B2 | 7/2011 | Kiani | |
| 2005/0197551 A1 | 9/2005 | Al-Ali et al. | |
| 2006/0241506 A1 | 10/2006 | Melker et al. | |
| 2006/0258921 A1 | 11/2006 | Addison et al. | |
| 2008/0066753 A1 | 3/2008 | Martin et al. | |
| 2008/0076992 A1 | 3/2008 | Hete et al. | |
| 2008/0167564 A1 | 7/2008 | Hete et al. | |
| 2008/0190430 A1 | 8/2008 | Melker et al. | |
| 2008/0262326 A1 | 10/2008 | Hete et al. | |
| 2009/0043179 A1 | 2/2009 | Melker et al. | |
| 2009/0069647 A1 | 3/2009 | McNames et al. | |
| 2009/0076399 A1 | 3/2009 | Arbel et al. | |
| 2011/0270094 A1 | 11/2011 | Kiani | |

FOREIGN PATENT DOCUMENTS

| | | |
|---|---|---|
| EP | 11179769.2 | 10/2005 |
| JP | 2006-508584 | 12/2006 |
| WO | WO 98/24489 | 6/1998 |

OTHER PUBLICATIONS

PCT/US04/00027, Patent Cooperation Treaty PCT International Search Report, Form PCT/ISA/210, pp. 1-2.

Hertzman, A.B., "The Blood Supply of Various Skin Areas as Estimated by the Photoelectric Plethysmograph," American Journal of Physiology, 124: 328-340, 1938.

Partridge, B.L., "Use of Pulse Oximetry as a Noninvasive Indicator of Intravascular Volume Status," Journal of Clinical Monitoring, 3(4): 263-8, 1987.

Shelly, Kirk H., et al.; "The Detection of Peripheral Venous Pulsation Using the Pulse Oximeter as a Plethysmograph," Journal of Clinical Monitoring, vol. 9 No. 4, pp. 283-287, 1993.

Shelly, K. H., et al., "Arterial-Pulse Oximetry Loops: A New Method of Monitoring Vascular Tone," Journal of Clinical Monitoring, 13: 223-228, 1997.

Johansson, A., "Estimation of Respiratory Volumes From the Photoplethysmographic Signal. Part I: Experimental Results," Medical & Biological Engineering& Computing, vol. 37, pp. 42-47, 1999.

Shamir, M., et al., "Pulse Oximetry Plethysmographic Waveform During Changes in Blood Volume," British Journal of Anaesthesia, 82 (2): 178-81, 1999.

Munis, James R. M.D., Ph.D., et al., "Peripheral Venous Pressure as a Hemodynamic Variable in Neurosurgical Patients," Anesthesia & Analgesia, 92: 172-9, 2001.

Amar, D., MD, et al., "Correlation of Peripheral Venous Pressure and Central Venous Pressure in Surgical Patients," Journal of Cardiothoracic and Vascular Anesthesia, vol. 15, No. 1, pp. 40-43, 2001.

Awad, A.. A., M.D., et al., "Different Responses of Ear and Finger Pulse Oximeter Wave Form to Cold Pressor Test," Technology, Computing and Simulation, Anesthesia & Analgesia, 92: 1483-6, 2001.

Awad, A.. A., M.D., et al., "How Does the Plethysmogram Derived From the Pulse Oximeter Relate to Arterial Blood Pressure in Coronary Artery Bypass Graft Patients?", Anesthesia & Analgesia, 93: 1466-71, 2001.

Weingarten, T. N., et al., "Peripheral Venous Pressure as a Measure of Venous Compliance During Pheochromocytoma Resection," Anesthesia & Analgesia, 99: 1035-7, 2004.

Shelly, Kirk, H., M.D., Ph.D., et al., "The Effect of Venous Pulsation on the Forehead Pulse Oximeter Wave Form as a Possible Source of Error in $Spo_2$ Calculation," Anesthesia & Analgesia., 100: 743-7, 2005.

Shelly, Kirk H., M.D., Ph.D., et al., "The Use of Joint Time Frequency Analysis to Quantify the Effect of Ventilation of the Pulse Oximeter Waveform," Journal of Clinical Monitoring and Computing, 7 pages, 2006.

Awad, A. A. M.D., et al., "Analysis of the Ear Pulse Oximeter Waveform," Journal of Clinical Monitoring and Computing, 20: 175-184, 2006.

Shelly, Kirk, H., M.D., Ph.D., et al., "What is the Best Site for Measuring the Effect of Ventilation of the Pulse Oximeter Waveform?", Technology, Computing, and Simulation, vol. 103, No. 2, Aug. 2006.

Gesquiere, Michael J., M.D., et al., "Impact of Withdrawal of 450 ML of Blood on Respiration-Induced Oscillations of the Ear Plethysmographic Waveform," Journal of Clinical Monitoring and Computing, 21: 277-282, 2007.

Shelly, Kirk H., M.D., Ph.D., "Photoplethysmography: Beyond the Calculation of Arterial Oxygen Saturation and Heart Rate," Anesthesia & Analgesia, vol. 105, No. 8, Aug. 2007.

Awad, A. A., M.D., et al., "The Relationship Between the Photoplethysmographic Waveform and Systemic Vascular Resistance," Journal of Clinical Monitoring and Computing, 8 pages, 2007.

Lu, Sheng, Ph.D., et al., "Can Photoplethysmography Variability Serve as an Alternative Approach to Obtain Heart Rate Variability Information?," Journal of Clinical Monitoring and Computing, 7 pages, 2007.

Jablonka, D. H., M.D., et al., "Comparing the Effect of Arginine Vasopressin on Ear and Finger Photoplethysmography," Journal of Clinical Anesthesia, 4 pages, 2008.

Micha Shamir, et al., *Plethysmographic Waveform Variation as an Indicator to Hypovolemia*, Anesthesia-Analgesia 2003; 97:602-603.

U.S. Appl. No. 12/568,311, filed Dec. 28, 2009.

Cournand, et al., Physiological Studies of the Effect of Intermittent Positive Pressure Breathing on Cardiac Output in Man, AmJ Physio 1948; 152:162-73.

Brecher, et al., Effect of Respiratory Movements on Superior Cava Flow Under Normal and Abnormal Conditions, Am J Physiol. 1953; 172:457-61.

Guyton, Determination of Cardiac Output by Equating Venous Return Curves With Cardiac Response Curves, Physiol Rev. 1955; 35:123-9.

Bartelstone, Role of the Veins in Venous Return, Circ Res. 1960; 8:1059-76.

Folkow, et al., Veins and Venous Tone, Am Heart J. 1964; 68:397-408.

Morgan, et al., The Homodynamic Effects of Changes in Blood Volume During Intermittent Positive-Pressure Ventilation, Anesthesiology 1969; 30:297-305.

Eustace, A Comparison Between Peripheral and Central Venous Pressure Monitoring Under Clinical Conditions, Injury 1970.

Zoller, et al., The Role of Low Pressure Baroreceptors in Reflex Vasoconstrictor Responses in Man, J Clin Invest. 1972; 51:2967-72.

Coyle, et al., Respiratory Variations in Systemic Arterial Pressure as an Indicator of Volume Status, Anesthesiology 1983; 59:A53.

Jardin, et al., Cyclic Changes in Arterial Pulse During Respiratory Support, Circulation 1983; 68:266-74.

Perel, et al., Systolic Blood Pressure Variation is a Sensitive Indicator of Hypovolemia in Ventilated Dogs Subjected to Graded Hemorrhage, Anesthesiology 1987; 67:498-502.

Pizov, et al., Systolic Pressure Variation is Greater During Hemorrhage Than During Sodium Nitroprusside-Induced Hypotension in Ventilated Dogs, Anesthesia & Analgesia 1988; 67:170-4.

Szold, et al., The Effect of Tidal Volume and Intravascular Volume State on Systolic Pressure Variation in Ventilated Dogs, Intensive Care Medicine 1989; 15:368-71.

Pizov, et al., The Use of Systolic Pressure Variation in Hemodynamic Monitoring During Deliberate Hypotension in Spine Surgery, Journal of Clinical Anesthesia 1990; 2:96-100.

Perel A, Cardiovascular Assessment by Pressure Waveform Analysis, ASA Annual Refresher Course Lecture 1991:264.

Vincent, et al., Cascular Reactivity to Phenylephrine and Angiotensin II: Comparison of Direct Venous and Systemic Vascular Responses, Clin Pharmocol Ther 1992; 51:68-75.

Rothe, Mean Circulatory Filling Pressure: Its Meaning and Measurement, J Appl Physiol. 1993; 74:499-509.

Lherm T, et al., Correlation Between Plethysmography Curve Variation ( Dpleth ) and Pulmonary Capillary Wedge Pressure ( Pcup ) in Mechanically Ventilated Patients , British Journal of Anesthesia 1995; Suppl. 1:41.

Murray, et al., The Peripheral Pulse Wave: Information Overlooked Journal of Clinical Monitoring, vol. 12, No. 5, 1996, pp. 365-377, XP009104503.

Dalen, et al., Is It Time to Pull the Pulmonary Artery Catheter?, JAMA 1996; 276:916-14.

Connors, et al., The Effectiveness of Right Heart Catheterization in the Initial Care of Critically Ill Patients, JAMA 1996; 276:889-97.

Rusch, et al., Signal Processing Methods for Pulse Oximetry, Computers in Biology and Medicine 1996; 26:143-59.

Ornstein, et al., Systolic Pressure Variation Predicts the Response to Acute Blood Loss, Journal of Clinical Anesthesia 1998; 10:137-40.

Stack Jr., et al., Spectral Analysis of Photoplethysmograms From Radial Forearm Free Flaps, Laryngoscope 1998; 108:1329-33.

Dorlas, et al., Photo-Electric Plythysmography as a Monitoring Device in Anaesthesia. Application and Interpretations, BR J Anaethesia 1999 82(2):178-81; A245, H188, H236.

Tyberg, How Changes in Venous Capacitance Modulate Cardiac Output, Pflugers Arch. 2002; 445:10-7.

Charalambous, et al., Comparison of Peripheral and Central Venous Pressures in Critically Ill Patients, Anaesth Intensive Care. 2003; 31:34-9.

Nilsson, Macrocirculation is Not the Sole Determinant of Respiratory Induced Variations in the Reflection Mode, Physiological Measurement [0967-3334] 2003; 24:935.

Tobias, et al., Measurement of Central Venous Pressure From a Peripheral Vein in Infants and Children, Pediatr Emerg Care. 2003; 19:428-30.

Bouchard, et al., Poor Correlation Between Hemodynamic and Echocardiographic Indexes of Left Ventricular Performance in the Operating Room and Intensive Care Unit, Crit Care Med, 2004; 32(3): p. 644-8.

Yamakage, et al., Can Variation of Pulse Amplitude Value Measured by a Pulse Oximeter Predict Intravascular Volume?, Anesthesiology 2004 abstracts.

Milhoan, et al., Upper Extremity Peripheral Venous Pressure Measurements Accurately Reflect Pulmonary Artery Pressures in Patients With Cavopulmonary or Fontan Connections, Pediatr Cardiol. 2004 ;25:17-9.

Desjardins, et al., Can Peripheral Venous Pressure Be Interchangeable With Central Venous Pressure in Patients Undergoing Cardiac Surgery?, Intensive Care Med. 2004; 30:627-32.

Hadimioglu, et al., Correlation of Peripheral Venous Pressure and Central Venous Pressure in Kidney Recipients, Transplant Proc. 2006; 38:440-2.

Hoftman, et al., Peripheral Venous Pressure as a Predictor of Central Venous Pressure During Orthotopic Liver Transplantation, J Clin Anesth. 2006; 18:251-5.

Mohrman, Cardiovascular Physiology. Table of Contents, 6th ed. New York: McGraw-Hill Medical; 2006.

Choi, et al., Can Peripheral Venous Pressure Be an Alternative to Central Venous Pressure During Right Hepatectomy in Living Donors?, Liver Transpl. 2007; 13:1414-21.

Baty, et al., Measurement of Central Venous Pressure From a Peripheral Intravenous Catheter Following Cardiopulmonary Bypass in Infants and Children With Congenital Heart Disease, J Intensive Care Med. 2008; 23:136-42.

Gunther, et al., Wavelet Analysis of Arterial Pressure and Blood Velocity Pulsatioins in the Aorta of Anesthetized Dogs, Biol. Res. 26: pp. 391-396, 1993.

Gunther, et al., Wavelet Analysis of Aortic Pulsations in Anesthetized Dogs: Effects of Spontaneous and Positive-Pressure Respiration, Journal of Biological systems, vol. 4, No. 1, pp. 45-59, 1996.

Jimenez et al., Continuous Wavelet Transform of Aortic Pressure Oscillations in Anesthetized Dogs: Effects of 45° Tilting, Biol. Res. 30: pp. 53-64, 1997.

Varanini et al., Spectral Analysis of Cardiovascular Time Series by the S-Transform, Computers in Cardiology 1997 Lund, Sweden Sep. 7-10, 1997, new York, NY, US, pp. 383-386.

Jimenez et al., Time-Frequency Analysis of Arterial Pressure Oscillations in Anesthetized Dogs: Effects of Standardized Hemorrhages, Shock (Philadelphia): Injury, Inflammation and Sepsis: Laboratory and Clinical Approaches, Lippincott Williams & Wilkins, US, vol. 15, No. 2, Feb. 1, 2001, pp. 143-150.

European Search Report dated Jan. 24, 2012.

* cited by examiner

Isolation of Peaks and Valleys

Baseline

500cc Blood Loss

1500cc Blood Loss

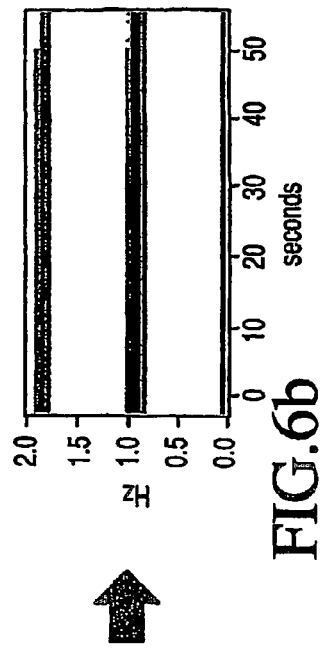
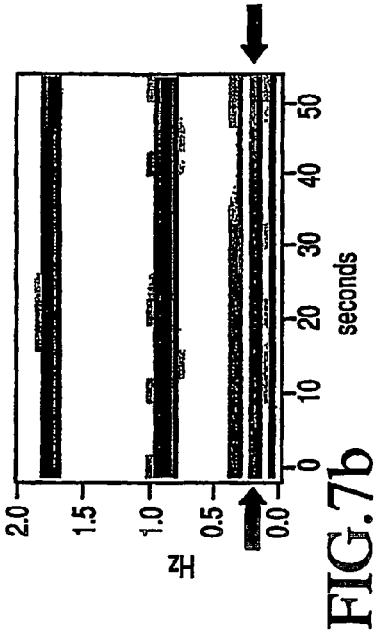
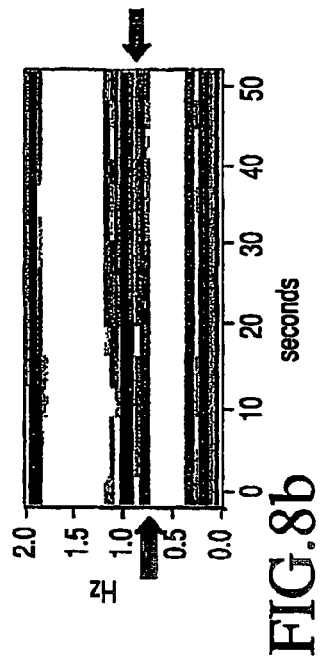
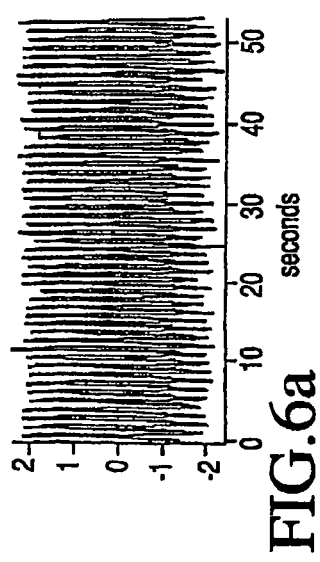
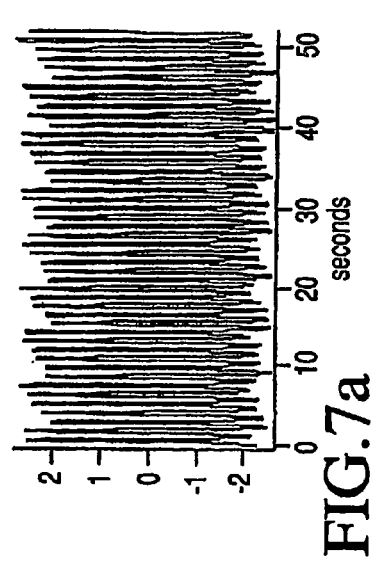
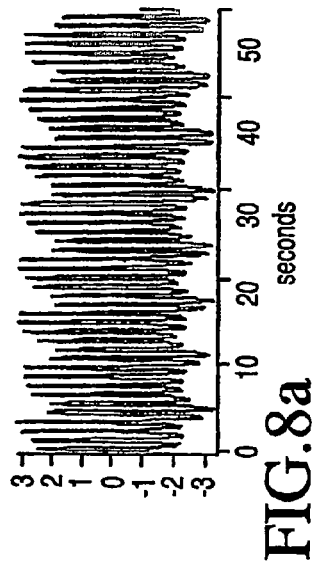

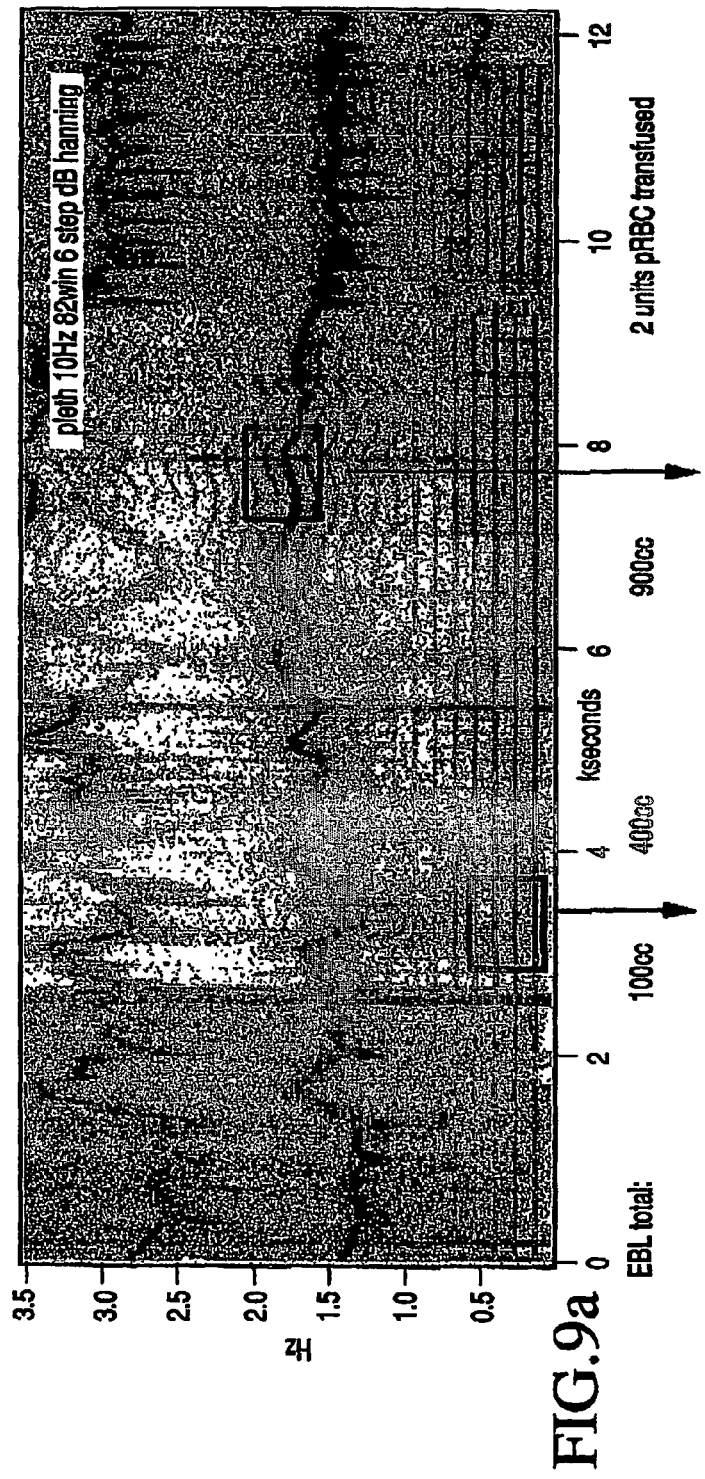
FIG. 9a
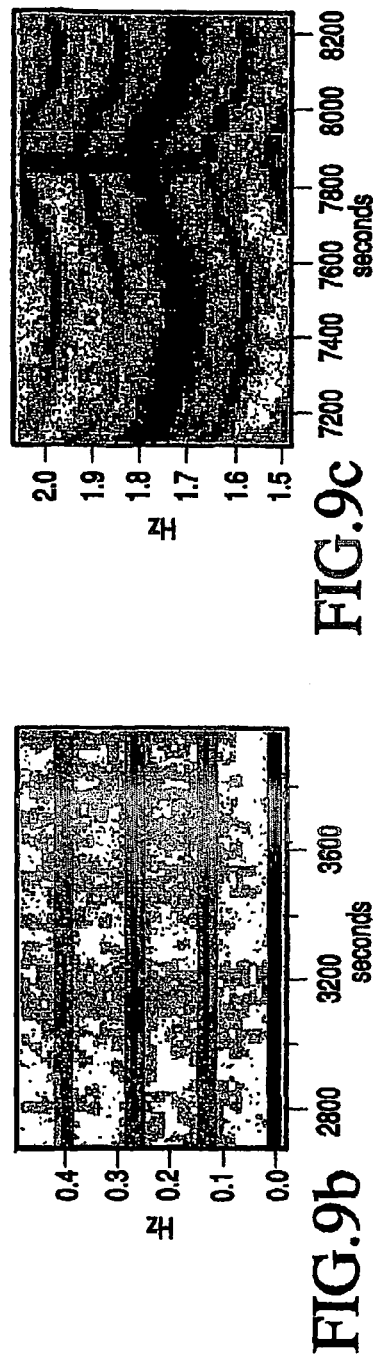
FIG. 9c
FIG. 9b

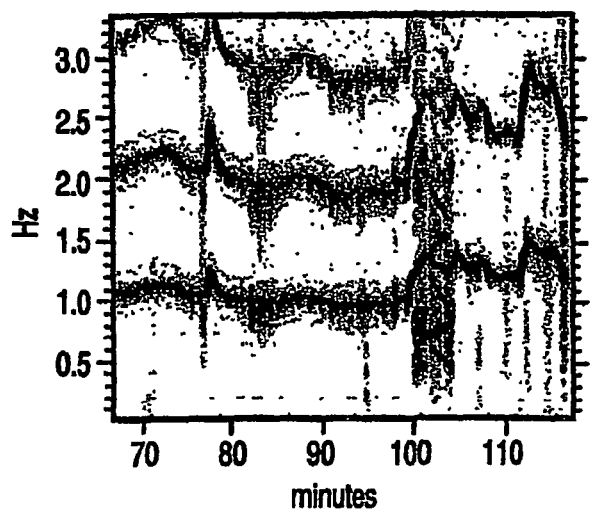
FIG.11a
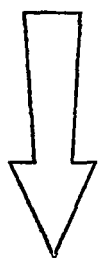
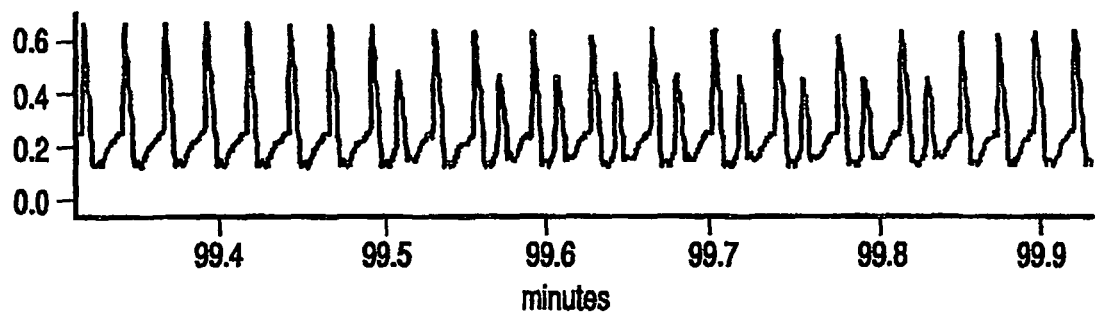
FIG.11b

Fourier Transformation of FIG.13A. Major peaks due to cardiac pulse. Minor peaks due to respiration.

Joint Time Frequency Analysis showing how the same FT changes with time.

Pleth after 300 cc EBL at High PAW

Detail of FIG.13B showing effect of ventilation on FT.

FIG.17
Reflective plethysmographic signal from three different sites (finger, ear, and forehead) from a supine patient.
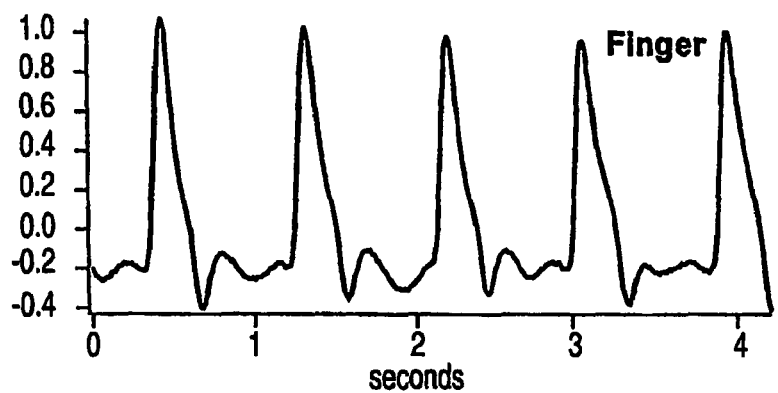
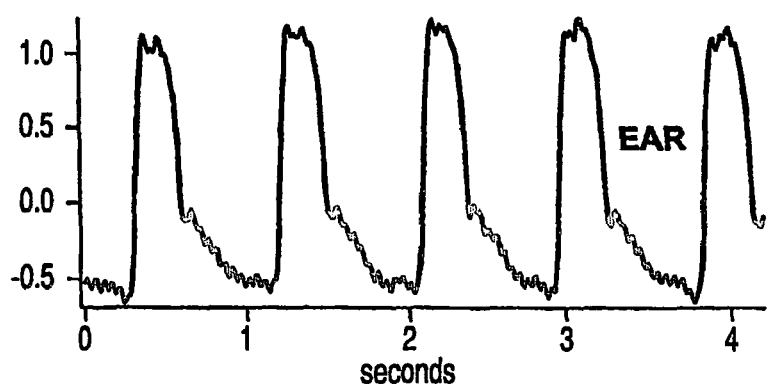
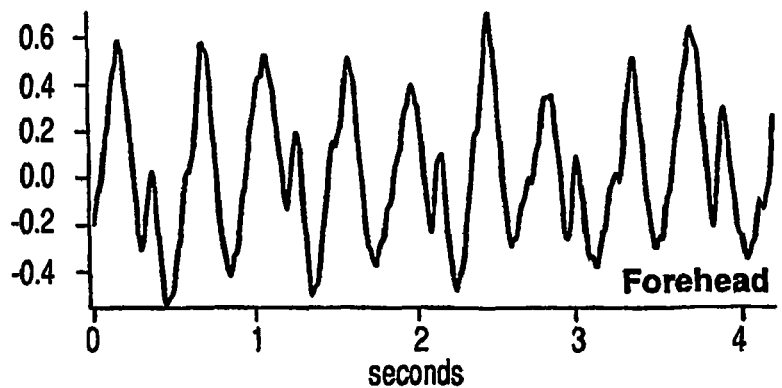

FIG. 18
The application of pressure to the forehead probe that obliterates the low pressure (venous or DC) component. This causes the tracing to more closely resemble the arterial tracing generated by an intra-arterial catheter.
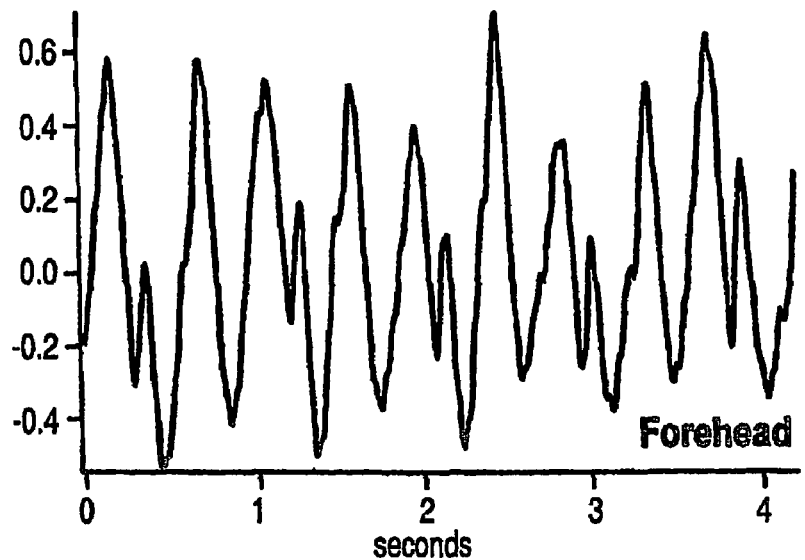
 Pressure dressing applied
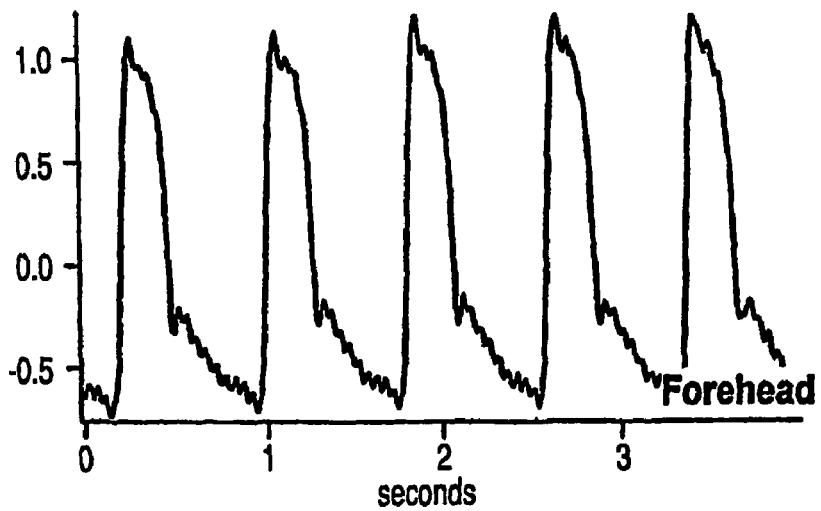

METHOD OF ASSESSING BLOOD VOLUME USING PHOTOELECTRIC PLETHYSMOGRAPHY

CROSS REFERENCE TO RELATED APPLICATIONS

The present application is the National Stage of International Application No. PCT/US2004/000027, filed Jan. 2, 2004, entitled "METHOD OF ASSESSING BLOOD VOLUME USING PHOTOELECTRIC PLETHYSMOGRAPHY", and claims the benefit of U.S. Provisional Application Ser. No. 60/465,609, filed Apr. 25, 2003, entitled "PULSE OXIMETER WAVEFORM ANALYSIS: DETERMINATION OF INTRAVASCULAR VOLUME STATUS" and U.S. Provisional Patent Application Ser. No. 60/454,048 filed, Mar. 12, 2003, entitled "PULSE OXIMETER WAVEFORM ANALYSIS".

BACKGROUND OF THE INVENTION

1. Field of the Invention

The invention relates to methods for studying and utilizing flow waveforms in the peripheral vasculature. In particular, the invention relates to a method for assessing blood volume by analyzing photoelectric plethysmographic waveforms of the pulse oximeter.

2. Description of the Prior Art

There is growing evidence that invasive monitors of volume status, such as the pulmonary artery catheter, may be a source of unacceptably frequent complications. Dalen J & Bone R, *Is it time to pull the pulmonary artery catheter?*, JAMA 1996; 276:916-14; Connors A, Speroff T & Dawson N, *The effectiveness of right heart catheterization in the initial care of critically ill patients*, JAMA 1996; 276:889-97. The potential loss of this important monitor from routine perioperative care necessitates the search for another means of monitoring a patient's blood volume status.

It has been known for quite some time that ventilation, and especially positive pressure ventilation, can have a significant impact on the cardiovascular system. Cournand A, Motley H, Werko L & Richards D, *Physiological studies of the effect of intermittent positive pressure breathing an cardiac output in man*, Am J Physiol 1948; 152:162-73; Morgan B, Crawford W & Guntheroth W, *The hemodynamic effects of changes in blood volume during intermittent positive-pressure ventilation*, Anesthesiology 1969; 30:297-305. The first formal studies of the effect of ventilator induced changes on the arterial pressure were done in the early 1980's. Coyle J, Teplick R. Long M & Davison J, *Respiratory variations in systemic arterial pressure as an indicator of volume status*, Anesthesiology 1983; 59:A53; Jardin F, Farcot J, Gueret P et al., *Cyclic changes in arterial pulse during respiratory support*, Circulation 1983; 68:266-74. This was soon followed by the intensive investigations of Azriel Perel. He coined the term "systolic pressure variation" to describe this phenomenon. Along with various co-investigators, his research has encompassed over twenty articles and abstracts on the topic. From this significant body of work, based on both animal and human data, a number of conclusions have been drawn.

The degree of systolic pressure variation is a sensitive indicator of hypo Perel A, Pizov R & Cotev S, *Systolic blood variation is a sensitive indicator of hypovelemia in ventilated dogs subjected to graded hemorrhage*, Anesthesiology 1987; 67:498-502. This variation is significantly better than heart rate, central venous pressure and mean systemic blood pressure in predicting the degree of hemorrhage which has occurred. Perel A, Pizov R & Cotev S, *Systolic blood pressure variation is a sensitive indicator of hypovelemia in ventilated dogs subjected to graded hemorrhage* Anesthesiology 1987; 67:498-502; Pizov R. Ya'ari Y & Perel A, *Systolic pressure variation is greater during hemorrhage than during sodium nitroprusside-induced hypotension in ventilated dogs*, Anesthesia & Analgesia 1988; 67:170-4. Chest wall compliance and tidal volume can influence systolic pressure variation. Szold A, Pizov R, Segal E & Perel A, *The effect of tidal volume and intravascular volume state on systolic pressure variation in ventilated dogs*, Intensive Care Medicine 1989; 15:368-71. Changes in systolic pressure variation correspond closely to changes in cardiac output. Ornstein E, Eidelman L, Drenger B et al., *Systolic pressure variation predicts the response to acute blood loss*, Journal of Clinical Anesthesia 1998; 10:137-40; Pizov R, Segal E, Kaplan L et al., *The use of systolic pressure variation in hemodynamic monitoring during deliberate hypotension in spine surgery*, Journal of Clinical Anesthesia 1990; 2:96-100.

Systolic pressure variation can be divided into two distinct components; Δup, which reflects an inspiratory augmentation of the cardiac output, and Δdown, which reflects a reduction in cardiac output due to a decrease in venous return. Perel A, *Cardiovascular assessment by pressure waveform analysis*, ASA Annual Refresher Course Lecture 1991:264. The unique value in systolic pressure variation lies in its ability to reflect the volume responsiveness of the left ventricle. Perel A, *Cardiovascular assessment by pressure waveform analysis*, ASA Annual Refresher Course Lecture 1991:264. In recent years, with the increased availability of the pulse oximeter waveform, similar observations have been made with this monitoring system. Partridge B L, *Use of pulse oximetry as a noninvasive indicator of intravascular volume status*, Journal of Clinical Monitoring 1987; 3:263-8; Lherm T, Chevalier T, Troche G et al., *Correlation between plethysmography curve variation (dpleth) and pulmonary capillary wedge pressure (pcup) in mechanically ventilated patients*, British Journal of Anesthesia 1995; Suppl. 1:41; Shamir M, Eidelman L A et al., *Pulse oximetry plethysmographic waveform during changes in blood volume*, British Journal Of Anaesthesia 82(2): 178-81 (1999). To date though, there has been remarkably little work done to document or quantify this phenomenon. Limitations of the aforementioned include:

1) Lack of a method of continuous measurement of the phenomenon.

2) Reliance on positive pressure and mechanical ventilation; and the requirement of ventilator maneuvers such as periods of apnea.

3) Lack of recognition of the venous contribution to the plethysmographic signal.

4) The lack of algorithms resistant to artifacts.

The pulse oximeter has rapidly become one of the most commonly used patient monitoring systems both in and out of the operating room. This popularity is undoubtedly due to the pulse oximeter's ability to monitor both arterial oxygen saturation as well as basic cardiac function (i.e. heart rhythm) non-invasively. In addition, it is remarkably easy to use and comfortable for the patient. The present invention attempts to expand upon the known usefulness of the pulse oximeter.

Pulse oximetry is a simple non-invasive method of monitoring the percentage of hemoglobin (Hb) which is saturated with oxygen. The pulse oximeter consists of a probe attached to the patient's finger or ear lobe, which is linked to a computerized unit. The unit displays the percentage of Hb saturated with oxygen together with an audible signal for each pulse beat, a calculated heart rate and in some models, a graphical display of the blood flow past the probe. Audible alms that can be programmed by the user are provided. A source of light originates from the probe at two wavelengths (e.g., 650 nm and 805 nm). The light is partly absorbed by hemoglobin, by amounts which differ depending on whether it is saturated with oxygen. By calculating the absorption at the two wavelengths the processor can compute the proportion of hemoglobin which is oxygenated. The oximeter is dependent on a pulsatile flow and produces a graph of the quality of flow. Where flow is compromised (e.g. by hypovolemia or vasoconstriction), the pulse oximeter may be unable to function. The computer within the oximeter is capable of distinguishing pulsatile flow from other more static signals (such as tissue or venous signals) to display only the arterial flow. Fearnley S J, *Pulse Oximetry*, Practical Procedures, Issue 5 (1995) Article 2.

In the process of determining oxygen saturation, the pulse oximeter functions as a photoelectric plethysmograph. In this role, it non-invasively measures minute changes in the blood volume of a vascular bed (e.g., finger, ear or forehead). The photoelectric plethysmograph is not a new invention. Hertzman A B, *The Blood Supply of Various Skin Areas as Estimated By the Photoelectric Plethysmograph*, Am. J. Physiol. 1938; 124:328-40. While the plethysmograph has been examined previously as a potential anesthesia monitoring device, remarkably little research has been done on this ubiquitous signal Dorlas J C & Nijboer J A, *Photo-electric plethysmography as a monitoring device in anaesthesia. Application and interpretation*, British Journal Of Anaesthesia 1985; 57:524-30.

It is important to understand that the typical pulse oximeter waveform presented to the clinician is a highly filtered and processed signal. It is normal practice for equipment manufactures to use both auto-centering and auto-gain routines on the displayed waveforms so as to minimize variations in the displayed signal. Despite this fact, the pulse oximeter waveform is still rich in information regarding the physiology of the patient. It contains a complex mixture of the influences of arterial, venous, autonomic and respiratory systems on the peripheral circulation. Key to the successful interpretation of this waveform is the ability to separate it into fundamental components.

Harmonic analysis (Fourier analysis) is one method of studying waveforms. It allows for the extraction of underlying signals that contribute to a complex waveform. A similar method has been used previously, with the pulse oximeter and photoelectric plethysmograph to improve the accuracy of the oxygen saturation measurement and to monitor tissue perfusion. Rusch T L, Sankar R & Scharf J E, *Signal processing methods for pulse oximetry*, Computers In Biology And Medicine 1996; 26:143-59; Stack B Jr, Futran N D, Shohet M N & Scharf J E, *Spectral analysis of photoplethysmograms from radial forearm free flaps*, Laryngoscope 1998; 108:1329-33.

In addition, it is previously know that photoelectric plethysmograph can be used to non-invasively measure minute changes in light absorption of living tissue. Hertzman, A B, *The Blood Supply of Various Skin Areas as Estimated By the Photoelectric Plethysmograph*, Am. J. Physiol. 124: 328-340 (1938). Rhythmic fluctuations in this signal are normally attributed to the cardiac pulse bringing more blood into the region being analyzed (i.e., finger, ear or forehead). This fluctuation of the plethysmographic signal is commonly referred to as the AC (arterial) component. The strength of the AC component can be modulated by a variety of factors. These factors would include stroke volume and vascular tone.

In addition to the cardiac pulse, there is a nonpulsatile (or weakly pulsatile) component of the plethysmography signal commonly referred to as the DC component. The DC component is the product the light absorption by nonpulsatile tissue. This would include fat, bone, muscle and venous blood.

Fluctuations in the photoelectric plethysmograph due to respiration/ventilation can also be detected. Johansson A & Oberg P A, *Estimation of respiratory volumes from the photoplethysmographic sit. Part I: Experimental results*, Medical And Biological Engineering And Computing 37(1): 42-7 (1999). These fluctuations have been used in the past in an attempt to estimate the degree of relative blood volume of patients undergoing surgery. Partridge B L, *Use of pulse oximetry as a noninvasive indicator of intravascular volume status*, Journal of Clinical Monitoring 3(4): 263-8 (1987); Shamir M, Eidelman L A et al., *Pulse oximetry plethysmographic waveform during changes in blood volume*, British Journal Of Anaesthesia 82(2): 178-81 (1999). Up until the development of the present invention, there has been a lack of recognition that respiratory signal modulates both the AC and DC components of the photo-plethysmograph.

With the foregoing in mind, it is apparent that a need exists for an improved method for efficiently and non-invasively monitoring the blood volume of a subject. The present invention attempts to achieve this goal by expanding upon the functionality of the pulse oximeter to provide a reliable, convenient and non-invasive mechanism for monitoring blood loss. In addition, the present invention provides new methods for extracting and utilizing information contained in a pulse oximeter waveform and other means of monitoring flow or pressure waveforms in the peripheral vasculature.

SUMMARY OF THE INVENTION

It is, therefore, an object of the present invention to provide a method for assessing blood volume within a subject. The method is achieved by generating a cardiovascular waveform representing physiological characteristics of a subject and determining blood volume of the subject by analyzing the cardiovascular waveform. In a preferred embodiment the steps of analyzing includes generating a first trace of the per heart-beat maximums of the cardiovascular waveform, which is representative of the systolic pressure upon the cardiovascular signal, generating a second trace of the per heart-beat minimums of the cardiovascular waveform, which is representative of the diastolic pressure upon the cardiovascular signal, and comparing the respective first trace and the second trace to generate an estimate of relative blood volume within the subject.

It is also an object of the present invention to provide a method for assessing blood volume within a subject wherein the method is achieved by generating a cardiovascular waveform representing physiological characteristics of a subject and determining blood volume of the subject by analyzing the cardiovascular waveform. The step of analyzing includes applying harmonic analysis to the cardiovascular waveform, extracting a frequency signal created by ventilation and applying the extracted frequency signal in determining blood volume of the subject.

It is another object of the present invention to provide a method for assessing a cardiovascular waveform. The method is achieved by generating a first trace of the per heart-beat maximums of the cardiovascular waveform, generating a second trace of the per heart-beat minimums of the cardiovascular waveform and comparing the respective first trace and the second trace to generate physiological characteristics of a subject.

It is a further object of the present invention to provide a method for assessing a cardiovascular waveform. The method is achieved by applying harmonic analysis to the cardiovascular waveform, extracting a frequency signal created by ventilation and applying the extracted frequency signal in determining physiological characteristics of a subject.

It is still another object of the present invention to provide a system for assessing blood volume within a subject. The system includes a probe adapted for retrieving cardiovascular waveforms of a subject and a processor associated with the probe for analyzing the retrieved cardiovascular waveforms. The processor includes means for determining blood volume of the subject by analyzing the cardiovascular waveform, wherein the step of analyzing includes generating a first trace of the per heart-beat maximums of the cardiovascular waveform, which is representative of the systolic pressure upon the cardiovascular signal, generating a second trace of the per heart-beat minimums of the cardiovascular waveform, which is representative of the diastolic pressure upon the cardiovascular signal, and comparing the respective first trace and the second trace to generate an estimate of relative blood volume within the subject.

It is yet a further object of the present invention to provide a system for assessing blood volume within a subject. The system includes a probe adapted for retrieving cardiovascular waveforms of a subject and a processor associated with the probe for analyzing the retrieved cardiovascular waveforms. The processor includes means for determining blood volume of the subject by analyzing the cardiovascular waveform, wherein the step of analyzing includes applying harmonic analysis to the cardiovascular waveform and extracting a frequency signal created by ventilation; and applying the extracted frequency signal in determining blood volume of the subject.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 6a and 6b show the transformation of a pulse oximeter waveform of a subject with normal blood volume via joint time-frequency analysis.

FIGS. 7a and 7b show the transformation of a pulse oximeter waveform of a subject with a moderate loss of blood volume via joint time-frequency analysis.

FIGS. 8a and 8b show the transformation of a pulse oximeter waveform of a subject with an acute loss of blood volume via joint time-frequency analysis.

FIGS. 9a, 9b and 9c respectively show the joint time-frequency analysis of a pulse oximeter waveform of a subject over time, a detailed view of the joint time-frequency analysis with blood loss of approximately 100 cc and a detailed view of the joint time-frequency analysis with blood loss in excess of 900 cc.

FIGS. 11a and 11b respectively show the joint time-frequency analysis and EKG of a subject with arrhythmia.

FIG. 17 is a reflective plethysmographic signal from three different sites (finger, ear, and forehead) from a supine patient.

FIG. 18 are graphs showing the application of pressure to the forehead probe that obliterates the low pressure (venous or DC) component. This causes the tracing to more closely resemble the arterial tracing generated by an intra-arterial catheter.

DESCRIPTION OF THE PREFERRED EMBODIMENTS

Figure 1A:
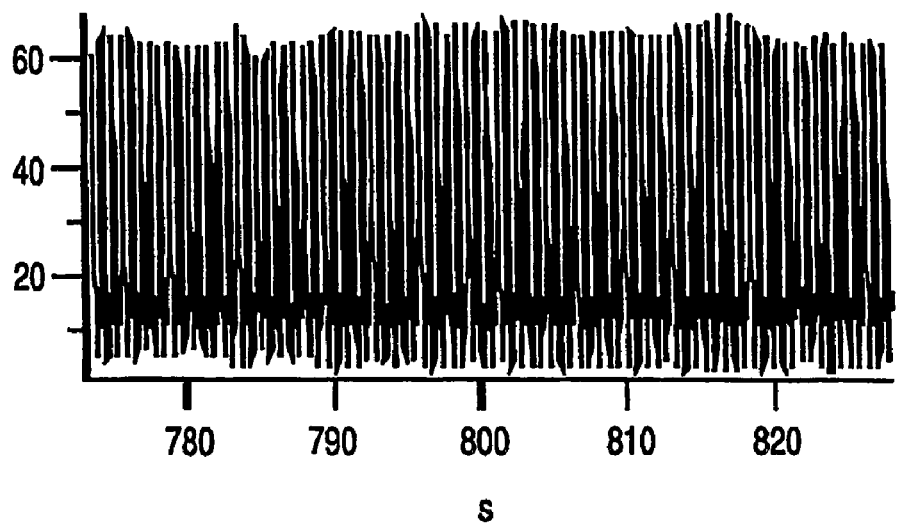
FIGS. 1a and 1b respectively show a baseline pulse oximeter waveform (FIG. 1a) vs. a pulse oximeter waveform exhibiting an acute blood loss effect (FIG. 1b).
Figure 1B:
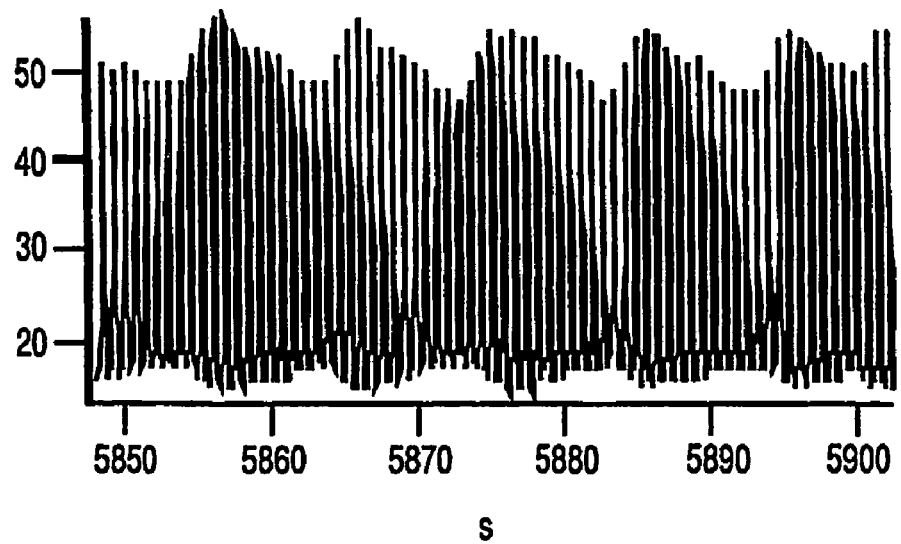

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1 to 5, and in accordance with a first embodiment of the present invention, a method for assessing blood volume through the analysis of a cardiovascular waveform, in particular, a pulse oximeter waveform, is disclosed. As the following disclosure will clearly demonstrate, the present invention monitors relative blood volume or effective blood volume. As such, the present method is preferably applied in analyzing blood volume responsiveness (that is, whether a patient needs to be given blood or other fluid).

In accordance with a preferred embodiment of the present invention, blood volume within a subject is monitored by using a pulse oximeter, or photoelectric plethysmograph, to first generate a pulse oximeter waveform representing physiological characteristics of a subject. The pulse oximeter waveform may also be considered a photoelectric plethysmographic waveform representing ventilation fluctuation of the subject. Those skilled in the art will understand that a photoelectric plethysmograph is a device used to estimate blood flow in a region of the body using photoelectric measurement techniques. In addition, those skilled in the art will understand that the present invention is described with reference to pulse oximeters, although other devices capable of measuring ventilation changes might be utilized in accordance with the present invention. For example, the concepts underlying the present invention could be utilized in conjunction with a strain gauge plethysmograph within the spirit of the present invention.

Analysis is achieved by generating a first trace of the local, that is, per heart-beat, maximums of the pulse oximeter waveform, which is representative of the systolic activities upon the blood volume, and generating a second trace of the local, that is, per heart-beat, minimums of the pulse oximeter waveform, which is representative of the diastolic activities upon the waveform (see FIGS. 2a, 2b, 2c, 3a, 3b, 5a and 5c). Thereafter, the amplitude and phase shift of the respective first trace and the second trace are compared to generate an estimate of blood volume within the subject.

Briefly, the first trace and the second trace are generated by recording the local maximums and local minimums of the pulse oximeter waveform during ventilation by the subject. In practice, a determination that the first trace and the second trace are in-phase with low amplitude is indicative of no blood loss, while the degree of phase shift and amplitude increase are indicative of increased blood loss.

This method of analyzing pulse oximeter, or photoelectric plethysmographic, waveforms allows for the separation of the venous and arterial contributions to the waveform. For example, during the time of moderate blood loss (or, more specifically moderate hypovolemia), the amplitudes of both the first trace of the local maximums and the second trace of the local minimums will increase proportionally to the degree of blood loss (see FIGS. 2b, 3a and 5a). For purposes of this discussion, this may be referred to as a "venous" response because it has a significant impact on the nonpulsatile component. With continued blood loss, the impact focuses upon the arterial system and the first and second traces go out of phase with oscillations of the local minimum traces occurring earlier than the oscillations of the local maximum traces (see FIGS. 2c, 3b and 5b). Analysis of these traces is done in such a way that the waveform may be used to determine a patient's effective blood volume, or more accurately, volume responsiveness.

Figure 4A:
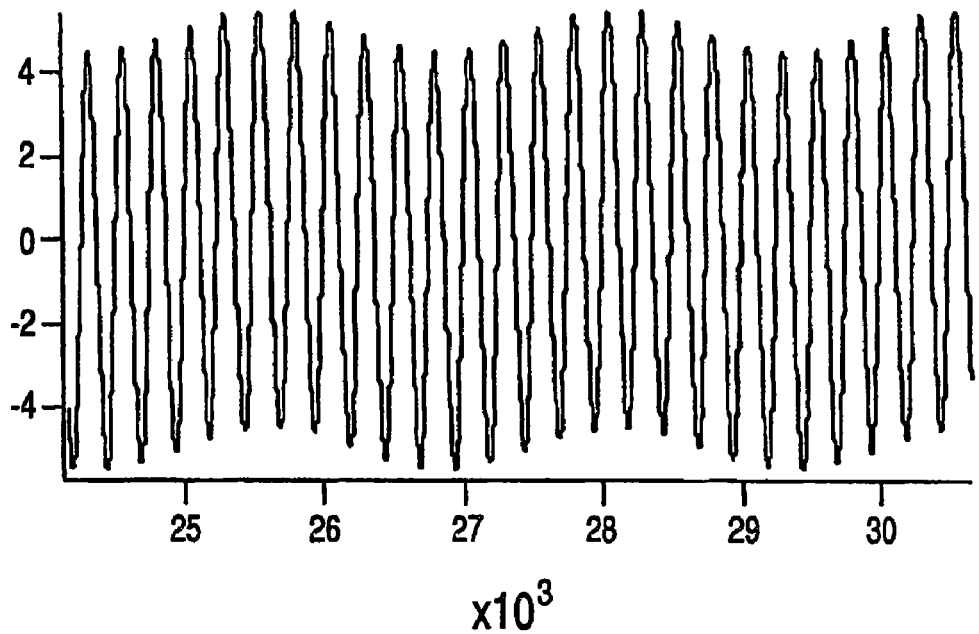
FIGS. 4a and 4b present idealized representations of pure venous signal (FIG. 4a) and pure arterial signal (FIG. 4b) extracted from the pulse oximeter waveform.
Figure 4B:
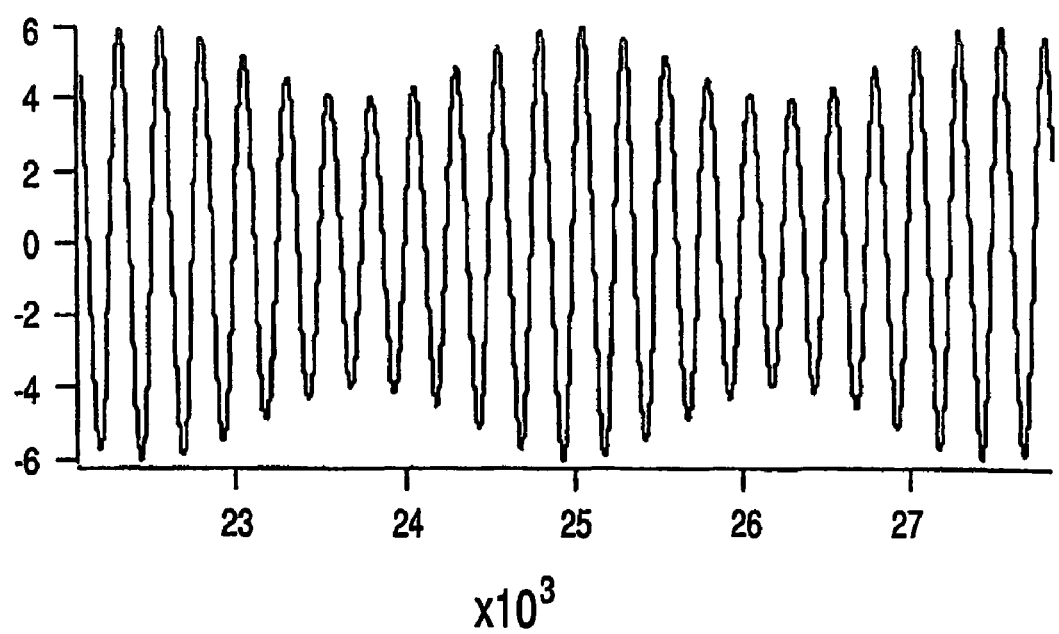

The difference between the venous response and the arterial response is shown in FIGS. 4a and 4b. In particular, FIGS. 4a and 4b respectively represent the venous component and the arterial component of the waveform shown in FIG. 1b; that is, the venous and arterial components of an individual who has lost a substantial amount of blood. The venous component as shown in FIG. 4a is derived by adding the peaks and troughs of the waveform and dividing the sum by two. Reference to FIG. 4a demonstrates the shift in venous blood taking place during ventilation. With regard to FIG. 4b, the arterial component is derived by subtracting the troughs from the peaks and dividing the remainder by two. FIG. 4b demonstrates that the loss of blood in the individual is so great that the individual is missing heartbeats.

This method of analysis distinguishes between the impact of ventilation on the arterial, pulsatile component (AC) (see FIGS. 2c, 3b, 4b and 5b) and the venous, nonpulsatile component PC) (see FIG. 2b, 3a, 4a and 5a) of the photoelectric plethysmograph. This is accomplished by creating first and second traces respectively based upon the local maximums and local minimums of the pulse oximeter waveform during ventilation by the subject. The first trace is generated based upon the local maximums (systolic) of the waveform and the second trace is generated based upon the local minimums (diastolic) of the waveform. The first and second traces are then superimposed and compared in regards to their amplitude and phase shift. As the amplitude and the phase shift of the two traces increase, the blood loss of the subject is known to be increasing.

Figure 2A:
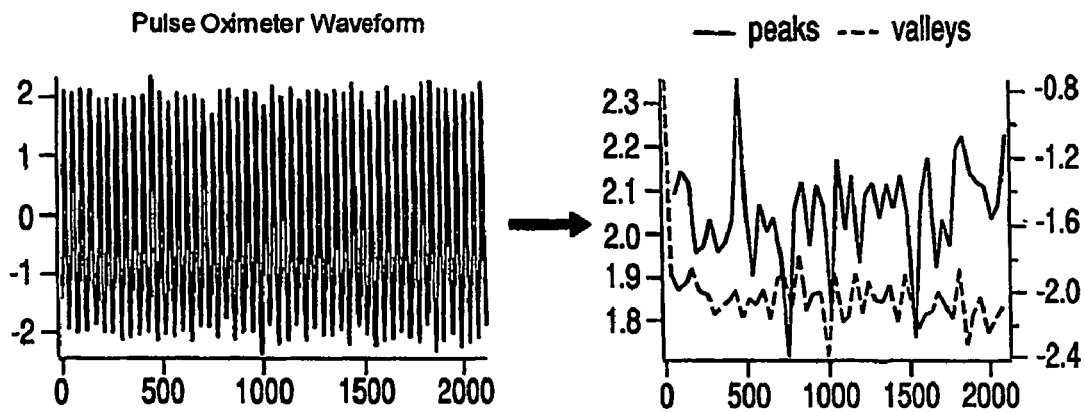
FIGS. 2a, 2b and 2c demonstrate the isolation of the local maximum and local minimum traces and their comparison during the different phases of blood loss.

In a normal patient, who has not suffered blood volume loss, the amplitudes of the local maximum and local minimum traces, first and second traces respectively, will be of relatively low amplitude and in-phase (see FIGS. 1a and 2a). During the time of "venous" loss, the amplitudes of both the local maximum and local minimum traces will increase positively related to the degree of blood loss (see FIGS. 2b, 3a and 5a). In fact, the amplitudes will continue to increase as the blood loss begins affecting the arterial system.

Figure 2B:
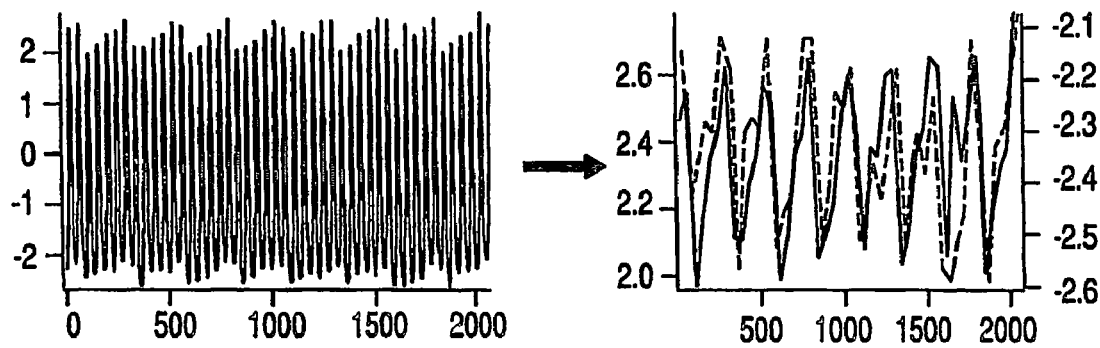
Figure 2C:
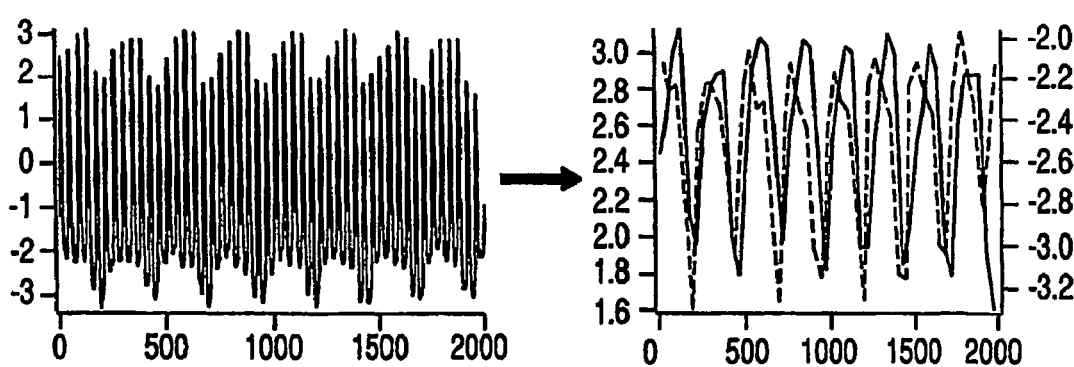
Figure 3A:
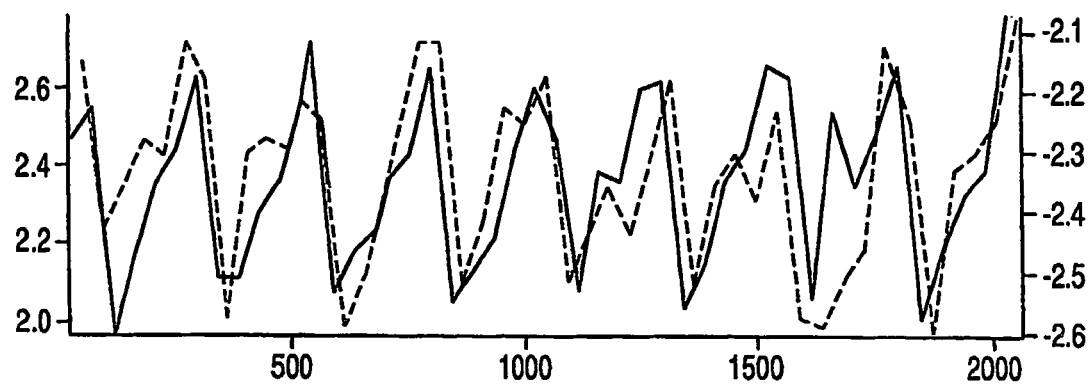
FIGS. 3a and 3b are detailed displays of the local maximum and local minimum traces demonstrating the phase shift with continued blood loss (solid lines=local maximums, broken lines=local minimums) with the upper graph FIG. 3a) representing venous impact and the lower graph (FIG. 3b) representing arterial impact.
Figure 3B:
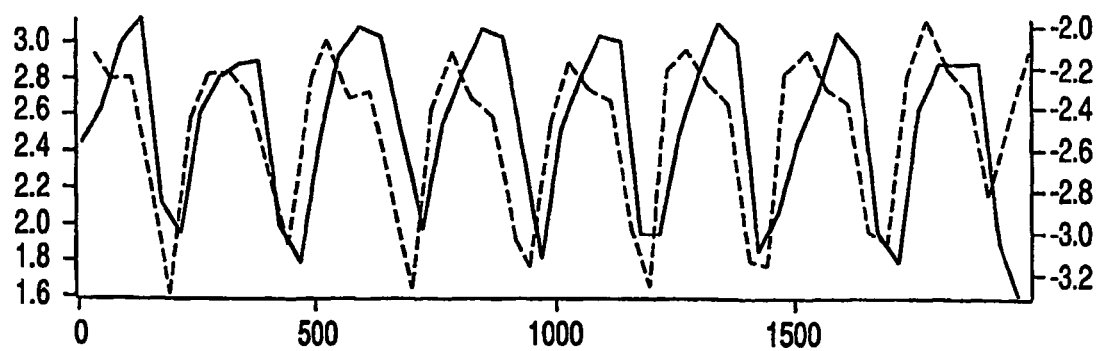
Figure 5A:
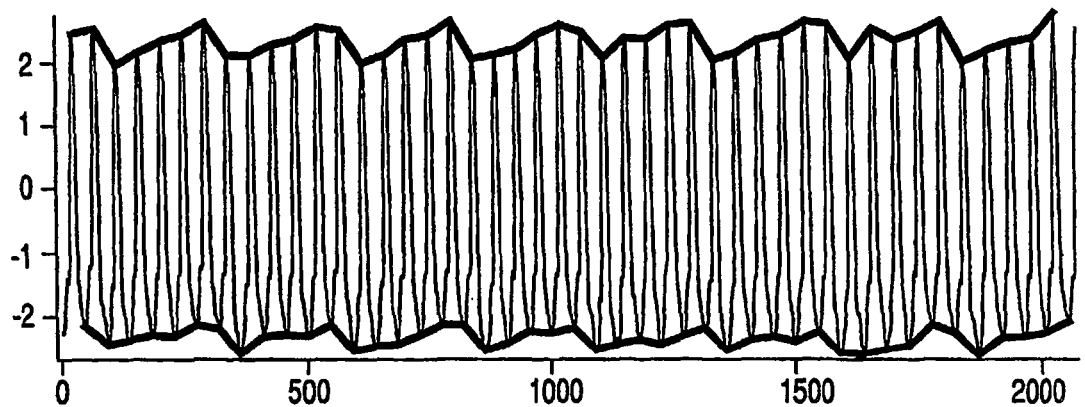
FIGS. 5a and 5b show respective displays of extracted local minimum and local maximum traces overlaid on the original pulse oximeter waveform. The upper graph FIG. 5a) demonstrates moderate blood loss effect (venous effect) and lower graph (FIG. 5b) demonstrates significant blood loss effect (arterial effect).
Figure 5B:
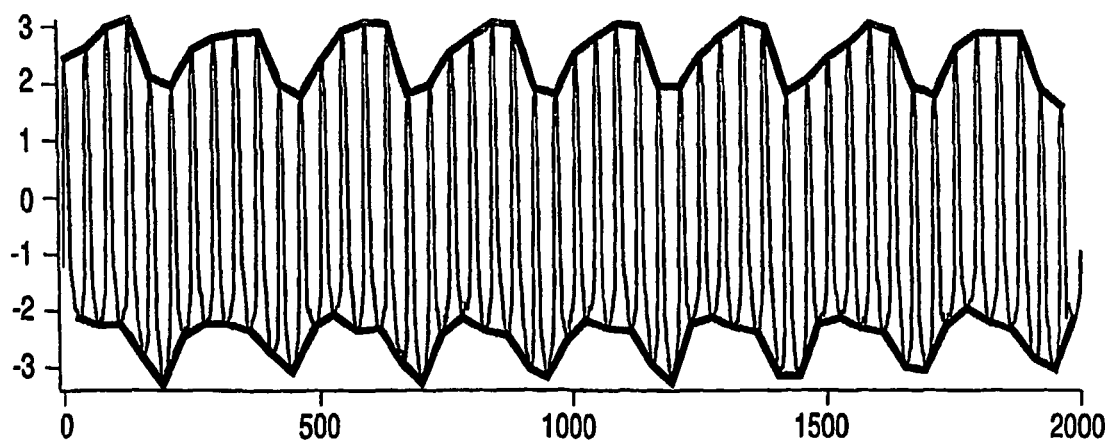

With continued blood volume loss, the two traces will go out of phase with the local minimum trace occurring earlier then the local maximum trace (see FIGS. 2c, 3b and 5b). The phase shift is not apparent until the blood loss begins affecting the arterial system. The degree of phase shift is proportional to the degree of impact the blood loss is having on cardiac output with each breath. If the local maximum trace occurs earlier than the local minimum trace this would indicate the patient is having ventilation augmentation of their cardiac output, a phenomenon that can occur with congestive heart failure.

These two measurements, the amplitude and phase shift of the local maximum and local minimum traces, taken together give an index of volume responsiveness of the patient. If the amplitudes are increased and phase shift has occurred, increasing the patient's blood volume through transfusion should increase the total cardiac output of the patient.

An additional measurement of the non-pulsatile component can be made by taking an average between the local maximum and local minimum. The degree of fluctuation of the average during a respiratory cycle corresponds inversely to pre-load (venous) volume; that is, the greater degree of fluctuation the lower the effective venous blood volume. An additional measurement of the pulsatile component (arterial) can be made by taking the difference between the local maximum and local minimum. The degree of fluctuation of the difference during a respiratory cycle corresponds directly degree of compromise of cardiac stroke volume due to low blood volume. The phase relationship between these two resulting waveforms can be used to determine the degree of ventilatory augmentation vs. dampening of the cardiac stroke volume.

The ability to mathematically separate the impact of ventilation on the arterial, (pulsatile component) and venous, (nonpulsatile component) allows one to assess the relative blood volume in two different regions of the vascular system (arterial and venous). The venous system blood volume is commonly referred to as the "pre-load". The pre-load directly impacts the amount of blood available to the heart before each contraction. The arterial system blood volume is commonly referred to as the "after-load". The after-load is a direct product of the cardiac output of the heart (stroke volume X heart rate). The sensitivity of this method can be increased by simultaneously measuring the airway pressure.

The present invention provides a method and apparatus for separating the impact of ventilation on the arterial and venous systems. This method is safe (compared to pulmonary artery catheters), noninvasive (compared to the use of dyes or radioactive isotopes), inexpensive (compared to TEE (transesophageal echocardiogram), requires no expertise for its use (unlike TEE) and no calibration is required. The clinician is presented with easy-to-understand numeric and a graphic display.

As those skilled in the art will certainly appreciate, it is desirable to provide clinicians with a warning regarding venous impact and an "alarm" when the blood loss has reach a quantity where it is affecting the arterial system. With this in mind, it is contemplated a display will provide the clinician with a basic numeric representation of blood loss and a waveform for a more studied evaluation of the patient's blood volume situation. The inclusion of a waveform with the basic numeric representation will provide the clinician with a way of evaluating the quality of the basic number provided in accordance with the present invention.

It is contemplated in accordance with a preferred embodiment that the invention may act as a dual level blood volume monitoring system. The venous component can act as part of an "early warning" system regarding the patient's blood volume status. As such, the present method would be employed in detecting the reduction in blood volume during the period of time that the body can still compensate. This is during a period of time the blood loss has not impacted yet on the cardiac stroke volume.

With further blood loss, the arterial component is impacted. This "alarm" phase would indicate that cardiac function is now being compromised by the loss of blood volume. Blood volume replacement therapy could then be guided by this dual level system.

As discussed above, the separation of the venous and arterial components is accomplished by recording the location of local maximums and local minimums of the predetermined pulse oximeter waveform during ventilation. A trace of the local maximums and a trace of the local minimums can then be superimposed and compared for relative amplitude and phase shift. Blood loss is determined as a function of amplitude and phase shift in the manner described above.

With regard to FIGS. 6 to 12, and in accordance with an alternate embodiment of the present invention, another method for assessing blood volume through the analysis of a cardiovascular waveform, in particular, a pulse oximeter waveform, is disclosed. In accordance with a preferred embodiment of the present invention, blood volume within a subject is monitored by first generating a pulse oximeter waveform representing physiological characteristics of a subject. The pulse oximeter waveform is generally a photoelectric plethysmographic waveform representing ventilation fluctuation of the subject. Thereafter, blood volume of the subject is determined by analyzing the pulse oximeter waveform or alternative means of monitoring cardiovascular waveforms.

Analysis is achieved by applying harmonic analysis to the pulse oximeter waveform, extracting a frequency signal created by ventilation, most commonly positive pressure ventilation, and applying the extracted frequency signal in determining blood volume of the subject. In accordance with a preferred embodiment of the present invention, the harmonic analysis is Fourier analysis, more particularly, joint time-frequency analysis. As those skilled in the art will certainly appreciate, joint time-frequency analysis is a common signal analysis tool utilized in studying frequency changes over time. In accordance with a preferred embodiment of the present invention, a short-time Fourier transform is employed, although other types of joint time-frequency analysis may be employed. In addition, the extraction of the frequency signal is achieved using a peak detection algorithm in the frequency range of ventilation.

As mentioned in the Background of the Invention, in the process of determining oxygen saturation, the pulse oximeter functions as a photoelectric plethysmograph. By analyzing how the frequency spectrum of the pulse oximeter waveform changes over time in accordance with the present invention, new clinically relevant features can be extracted.

Referring to FIGS. 6a and 6b, a pulse oximeter waveform is shown with an associated frequency spectrum generated based upon joint time-frequency analysis which breaks down the complex signals of the pulse oximeter waveform into its underlying sine and cosine waves. The signals shown in FIGS. 6a and 6b are representative of a patient before any blood loss. In particular, FIG. 6b shows the minimal respiratory signal that results from fluctuation in the venous system, while the signal at approximately 1 Hz results from the patient's base heart rate. FIG. 6b shows that, for the given gray scale, there is no detectable signal at the respiratory frequency (between 0.15 and 0.20 Hz).

Referring to FIGS. 7a and 7b, the signals generated for a subject encountering moderate blood loss only affecting the venous system (pre-load) are shown. FIG. 7b shows an increase in the signal from the respiratory frequency (such that it is now detectable, indicative of the change in blood volume affecting the shifting of venous blood during ventilation.

Now referring to FIGS. 8a and 8b, the signals generated for a subject encountering acute blood loss are shown. With reference to FIG. 8b, please note the different frequency spectrums of the joint time-frequency analysis as compared with that of the analysis shown in FIG. 6b. FIG. 8b shows an increase in the signal from the respiratory frequency indicative of the change in blood volume affecting the shifting of venous blood during ventilation and the development of secondary harmonics about the base heart rate signal (or cardiac pulse harmonic) resulting from the increased blood loss affecting the arterial system (stroke volume) of the subject.

The effects of increased blood loss are further demonstrated with reference to FIGS. 9a, 9b and 9c. Specifically, FIG. 9a is the joint time-frequency analysis of a pulse oximeter waveform of a subject as continued blood loss is encountered. As is shown in FIG. 9b, the joint time-frequency analysis reveals changes in the strength of the signal at the respiratory frequency with the development of harmonics when there is a blood loss of approximately 300 cc (indicative of changes in the venous component). This emergence of the respiratory band is similar to that shown in FIG. 7b.

The joint time-frequency analysis of the pulse oximeter waveform produces secondary harmonics surrounding the cardiac pulse harmonic, or primary harmonic, at a continuous blood loss of greater than 900 cc (indicative of changes in the arterial component). The development of similar secondary harmonics about the cardiac pulse harmonic of approximately 1 Hz is similarly shown in FIG. 8b.

As a result of these differing changes the pulse oximeter waveform, which are discerned via the application of joint time-frequency analysis, arterial and venous components of blood volume may be ascertained from the joint time-frequency analysis of the pulse oximeter waveform. Specifically, by monitoring shifts in the frequency baseline as manifested in the joint time-frequency analysis of the pulse oximeter waveform, one is able to monitor venous blood volume in accordance with the present invention (see FIG. 9b). The impact on cardiac output may be monitored by noting the development of secondary harmonics surrounding the cardiac pulse harmonic (see FIG. 9c). Such secondary harmonics are not present in a normal person, but might be present in a dehydrated individual although a medical practitioner would certainly be capable of determining whether the noted secondary harmonics are a result of blood loss or dehydration.

Figure 10:
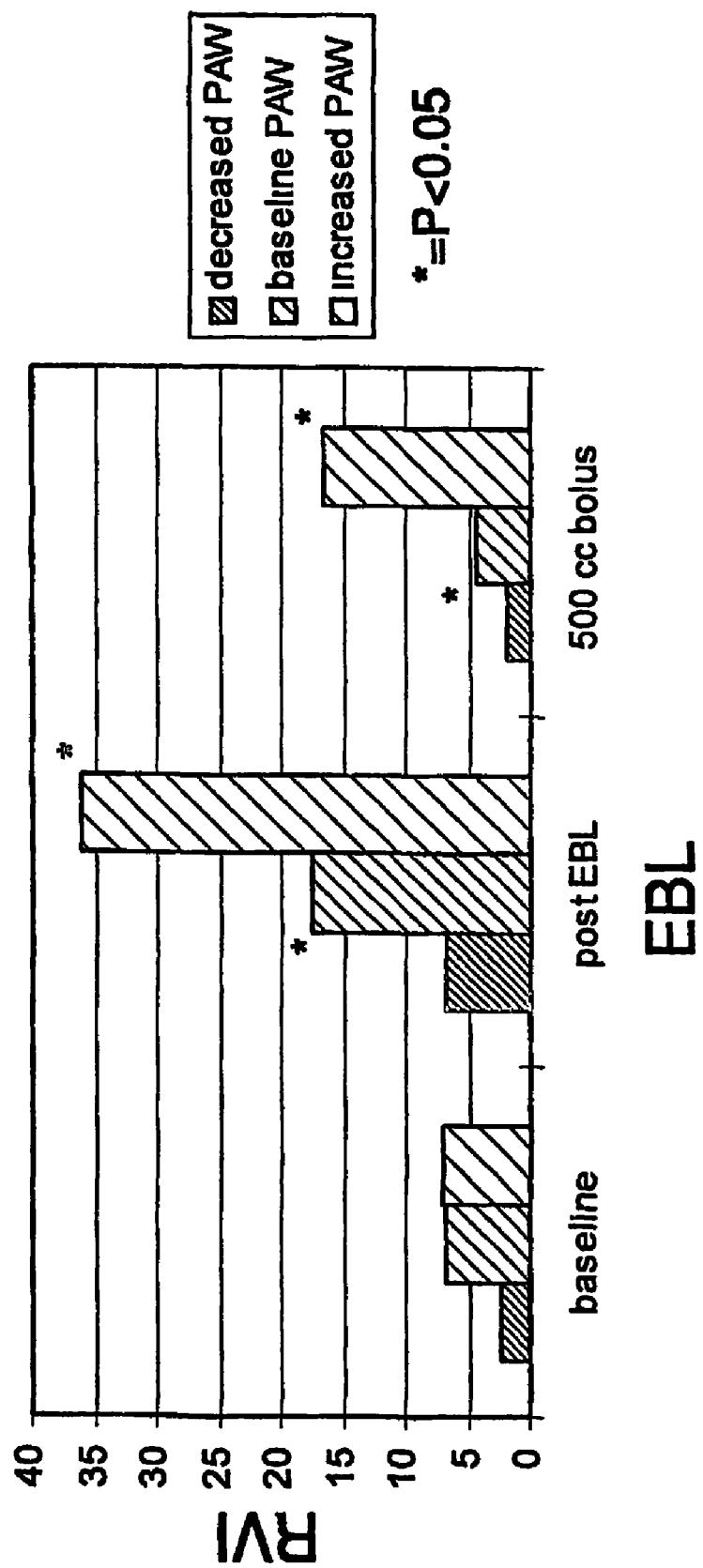
FIG. 10 is a chart of testing performed in accordance with the present invention. The chart shows the fluctuation in the pulse oximeter waveform (RVI) related to intraoperative bleeding (EBL) and peak airway pressure (PAW).
Figure 12A:
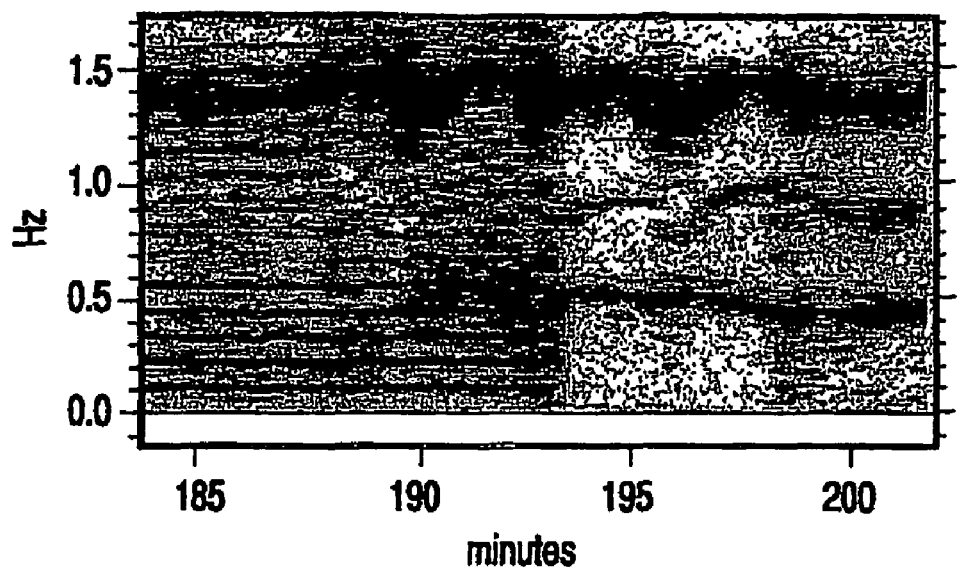
FIGS. 12a and 12b respectively show joint time-frequency analysis and airway pressure.
Figure 12B:
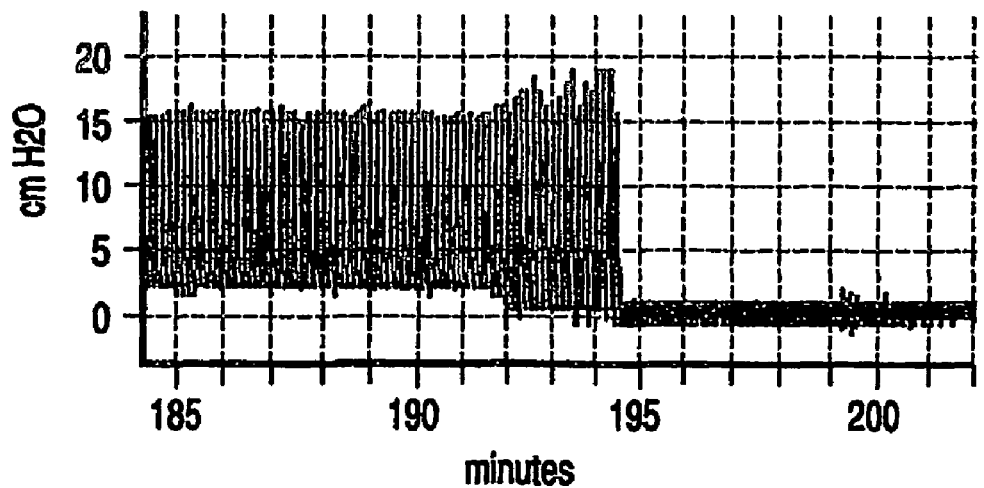
Figure 13B:
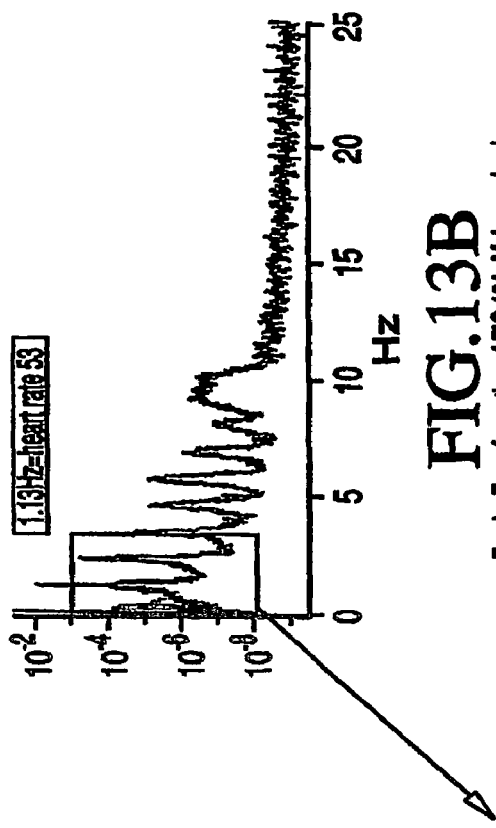
FIG. 13 demonstrates the construction of a joint time-frequency analysis from a pulse oximeter (photoelectric plethysmograph) waveform. The graphs also demonstrate the manner in which cardiac pulse rates and respiratory rates may be extracted from the analysis.
Figure 13D:
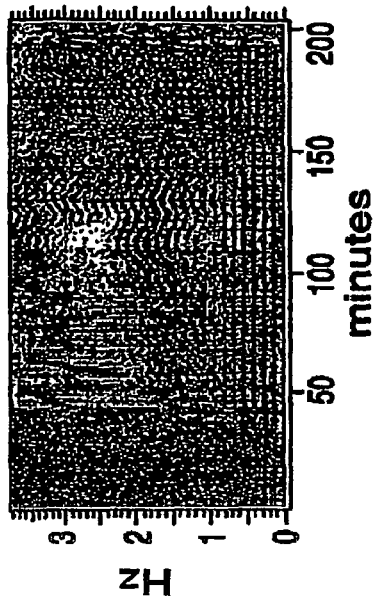
Figure 13A:
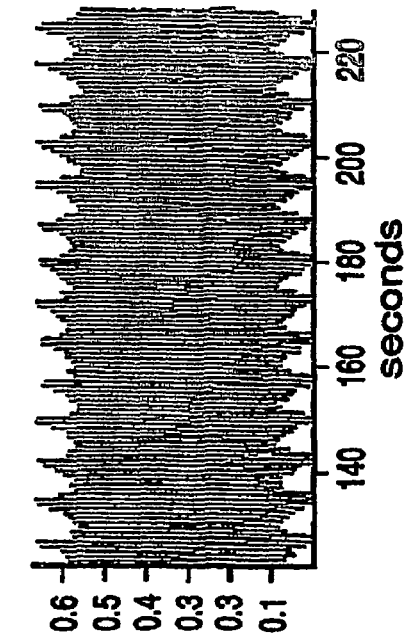
Figure 13C:
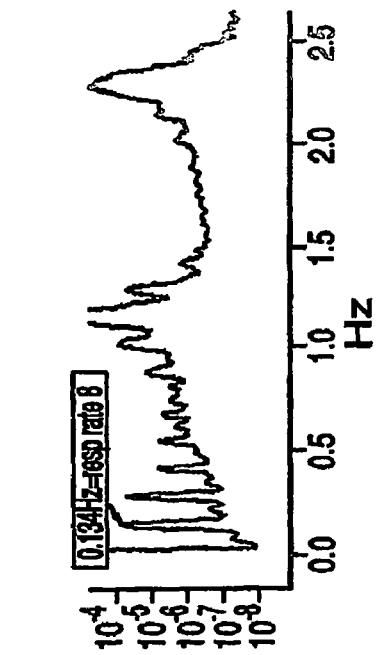

The result of the application of the present analysis technique to 8 patients is shown in FIG. 10.

The concepts underlying the present invention were tested upon thirty patients undergoing abdominal surgery by collecting their pulse oximeter waveforms, airway pressure and exhaled $CO_2$ waveforms (50 Hz). The pulse oximeter waveforms were analyzed with a short-time Fourier transform using a moving 4096 point Hanning window of 82 seconds duration. The frequency signal created by positive pressure ventilation was extracted using a peak detection algorithm in the frequency range of ventilation (0.08-0.4 Hz=5-24 breaths/minute). The respiratory rate derived in this manner was compared to the respiratory rate as determined by $CO_2$ detection. In total, 52 hours of telemetry data were analyzed. The respiratory rate measured from the pulse oximeter waveform in accordance with the present joint time-frequency analysis was found to have a 0.87 linear correlation when compared to $CO_2$ detection and airway pressure change. The signal strength increased in the presence of blood loss.

Despite the success of the present method as tested through comparison with $CO_2$ detection, it was found that cardiac arrhythmia (i.e. atrial fibrillation & frequent premature atrial and ventricular contractions) proved to be the primary cause of failure of this technique. As shown in FIGS. 11a and 11b, an irregular heart rhythm created a highly distinctive signal when joint time-frequency analysis was applied to the pulse oximeter waveform.

More particularly, 30 patients undergoing abdominal hysterectomy under general anesthesia had their pulse oximeter waveform, airway pressure and $CO_2$ waveform collected. As a part of their anesthetic, all patients were intubated after an induction with propofol and vecuronium. Anesthesia was maintained with nitrous oxide (60%-70%) and isoflurane (1%-2%). The ventilator was set to a tidal volume of 10 cc/kg at an inspiratory to expiratory (I:E) ratio of 1:2. During the surgery, estimated blood loss was closely followed and recorded, as well as replacement fluid given to the patient. Three times during the surgical procedure the ventilator was adjusted. This adjustment consisted of increasing the tidal volume until the peak pressure airway pressure was increased above baseline by 10 cm $H_2O$ (to maximum of 35 cm $H_2O$). This higher setting was maintained for 5 mins and then returned to baseline.

The data were collected using a computer acquisition system consisting of a 16-bit A-to-D PC card (DAQCard AI-16XE-50, National Instruments, Austin, Tex.) sampling at 50 Hz. BioBench (Version 1.0, National Instruments, Austin, Tex.) was the software used for the acquisition process. Waveform analysis was accomplished with Igor Pro (Version 3.14, WaveMetrics, Inc. Lake Oswego, Oreg.).

The pulse oximeter waveform was collected with a clinical pulse oximeter (OxiPleth Model 520A, Novametrics, Wallingford, Conn.) using a standard finger probe. The pulse oximeter had its auto-gain function disabled. The pulse oximeter waveform collected consists of the AC portion of inverted infrared signal (approximate 940 nm). The airway pressure and $CO_2$ were obtained from an Ohmeda RGM gas monitor (model 5250, Datex-Ohmeda, Madison Wis.).

The pulse oximeter waveform was analyzed with a short-time Fourier transform using a moving 4096 point Hanning window of 82 seconds duration. The frequency signal created by positive pressure ventilation was extracted using a peak detection algorithm in the frequency range of ventilation (0.08-0.4 Hz). The respiratory rate was derived in this manner and was confirmed by to the respiratory rate as detected by $CO_2$ production. This was used as the gold standard for comparison purposes.

More particularly, and in accordance with a preferred embodiment of the present invention, the joint time-frequency analysis of the pulse oximeter waveform is created in the following manner. The pulse oximeter waveform is converted to a numeric series by analog to digital conversion with sampling of the continuous pulse oximeter output at a rate of 50 Hz. The sampled waveform is collected into a digital buffer, presently 4096 points—82 seconds. A windowing function is used on the data in the digital buffer (presently Hanning window is used in accordance with a preferred embodiment of the present invention). The windowing function is designed to minimize the effect of the finite range of the sample set.

A Fourier transform is then preformed on the data set in the digital buffer. The data are expanded in a logarithmic fashion. The logarithmic expansion, an optimal step, is done to compensate for the otherwise overwhelming signal strength for the heart rhythm. The result is transferred to a display buffer. The digital buffer then accepted new data from the pulse oximeter on a first-in, first-out basis. The amount of new data added is determined by respiratory rate measured up to that point. Specifically, the amount of data associated with the time of one breath is added to buffer. This new data was then analyzed by the method outlined in accordance with the "windowing function" step and the Fourier analysis step described above.

The resulting data are then plotted with Y axis—frequency & X axis—time. A number of different techniques can be used to display the results (false color, gray scale, "waterfall" or as a surface plot), without departing from the spirit of the present invention.

In total, 52 hours of telemetry data were analyzed. The respiratory rate measured from the pulse oximeter waveform had a 0.89 linear correlation (Pearson coefficient of correlation) when compared to $CO_2$ detection as a method of detecting ventilation. Further analysis was done using the method described by Bland and Altman. Bland J M & Altman D G, *A note on the use of the intraclass correlation coefficient in the evaluation of agreement two methods of measurement*, Computers In Biology And Medicine 1990; 20:337-40. The differences between each pair of values obtained using the two different methods were plotted as the Y-axis, whereas the averages of the each pair of values obtained using the two different methods were plotted as the X-axis. The mean (bias), standard deviation (SD) [as a measure of precision], and the upper and lower limits of agreement were calculated. The bias was 0.03 breath/min, SD was 0.557 breath/min and the upper and lower limits of agreement were 1.145 and −1.083 breath/min respectively.

As mentioned above, review of the data generated after joint time-frequency analysis revealed that the presence of cardiac arrhythmia (i.e. atrial-fibrillation & frequent PVC/PAC) proved to be the primary cause of failure of the present methodology.

Analysis of the data generated as a result of the joint time-frequency analysis revealed two factors that appeared to influence the strength of the respiratory signal contained in the pulse oximeter waveform; 1) the airway pressure (see FIGS. 12a and 12b) and 2) the blood volume status of the patient (see FIGS. 9a, 9b and 9c). For any given patient, higher airway pressures resulted in a stronger respiratory signal (p<0.01 using paired student T-test). In addition, it was observed that as significant blood loss (>300 cc EBL) occurred during a surgical procedure (seen in 8 cases), the respiratory signal would increase strength to only return to baseline as fluid replacement was given. The present method of harmonic analysis also appears to be useful in detecting spontaneous ventilation occurring at the end of the procedures (see FIGS. 12a and 12b).

Further and with reference to FIG. 13, there were a number of features noted in the joint time-frequency analysis of pulse oximeter that, while not formally studied, were nevertheless interesting. The pulse rate is given by the frequency of the primary harmonic, or cardiac pulse harmonic (i.e., 1.13 Hz=68 beats/min). The thickness of the primary harmonic band of the joint time-frequency analysis corresponds to the heart rate variability (narrow ~low heart rate variability, wide ~high heart rate variability).

Ventilation was observed to have two distinct impacts on the pulse oximeter waveform as seen through joint time-frequency analysis. The most commonly seen was a shift of the baseline with each breath. The baseline of the pulse oximeter waveform is often considered to reflect the DC component of the pulse oximeter waveform. Shifts in the baseline are felt to be associated with changes in the venous bed (non pulsatile blood). Dorlas J C & Nijboer J A, Photo-electric plethysmography as a monitoring device in anaesthesia, Application and interpretation, British Journal Of Anaesthesia 1985; 57:524-30. This type of DC modulation was observed in all studied patients during both periods of controlled and spontaneous ventilation. As such, by monitoring shifts in the baseline as manifested in the joint time-frequency analysis, one is able to monitor venous blood volume accordance with the present invention (see FIG. 9b).

The less commonly seen phenomenon was a change of the amplitudes of the pulse beats (AC component or arterial pulsatile component) with each breath in the joint time frequency analysis. This type of AC modulation has been associated with hypovolemic states. Shamir M, Eidelman L A, Floman Y et al., Pulse oximetry plethysmograph waveform during changes in blood volume, British Journal Of Anaesthesia 1999; 82:178-81; Partridge B L, Use of pulse oximetry as a noninvasive indicator of intravascular volume status, Journal of Clinical Monitoring 1987; 3:263-8. In accordance with the present invention, it have been noted that recurrent changes in the amplitude of the pulse beat are manifested on the joint time-frequency analysis as secondary harmonics surrounding the cardiac pulse harmonic. The distance between the secondary harmonics and the cardiac pulse harmonic is proportionally linked to the respiratory rate. These secondary harmonics were present in all patients (eight) who had more then a 300 cc blood loss. As such, and in accordance with the present invention, the arterial blood volume may be monitored by noting secondary harmonics surrounding the cardiac pulse harmonic of the joint time-frequency analysis (see FIG. 9c).

Joint time-frequency analysis allows for the extraction of the underlying frequencies that make up a signal and to observe how these underlying waveforms change over time. In the case of the pulse oximeter, the plethysmographic waveform that is displayed is a highly processed and filtered signal but is still rich in physiologic information. As would be expected, the cardiac pulse waveform is the predominant signal present in pulse oximeter signal. The respiratory component, when present, can be subtle and difficult to monitor using conventional display methods. When the same waveform is displayed in the frequency domain (i.e., using joint time-frequency analysis), the respiratory effect is easy to follow. The two most common reasons for inaccurate readings appeared to be motion artifact and irregular heartbeats.

In practice, joint time-frequency analysis of the pulse oximeter waveform offers a variety of advantages. In particular, it provides for isolation of the respiratory induced changes of the pulse oximeter, which may be related to intra-vascular blood volume. It also allows for separation of the venous and arterial components (AC &DC) of respiratory variability, allowing for a unique detailed analysis of the impact of blood volume on cardiac function (pre-load vs. after-load effects). Joint time-frequency analysis also provides a method to determine respiratory rate (both controlled and spontaneous) (see FIG. 13 wherein minor peaks of the frequency spectrum are due to respiration), detecting spontaneous breathing patterns, detecting irregularity of heart rate, allowing for the determination of heart rate and estimating heart rate variability by the examination of the width of the primary cardiac pulse harmonic. The analysis also provides a method of displaying a large volume of pulse oximeter waveform information in a small area. (Three or more hours of data collection easily fits on one page). In addition, the present method is resistant to isolated artifacts.

In implementing the present invention, it is contemplated various limitation may be encountered and various concepts are ripe for further consideration. Specifically, the following clinical conditions may either preclude the use of this technique or greater limit its applicability: cardiac arrhythmia such as atrial fibrillation or frequent premature ventricular beats; (which causes a beat to beat variation in the pulse waveform amplitude); excessive ventilator tidal volumes or reduced chest wall compliance would have to be taken into account; or in conditions of low cardiac output (EF<30%) the potential exists for augmentation of the ventricular output ($\Delta$up).

The present invention provides for the development of an algorithm that generates an easily understood and clinically relevant numeric index of respiratory variability. Such an index could then be used to non-invasively monitor the fluid status of patients undergoing surgical procedures. This development is part of a larger on-going project to better understand and utilize the pulse oximeter waveform. It is hoped that from this work the next generation of pulse oximeters will be designed to improve clinical monitoring. These improvements could allow for the non-invasive monitoring of volume status, vascular tone and tissue oxygen extraction.

Figure 14:
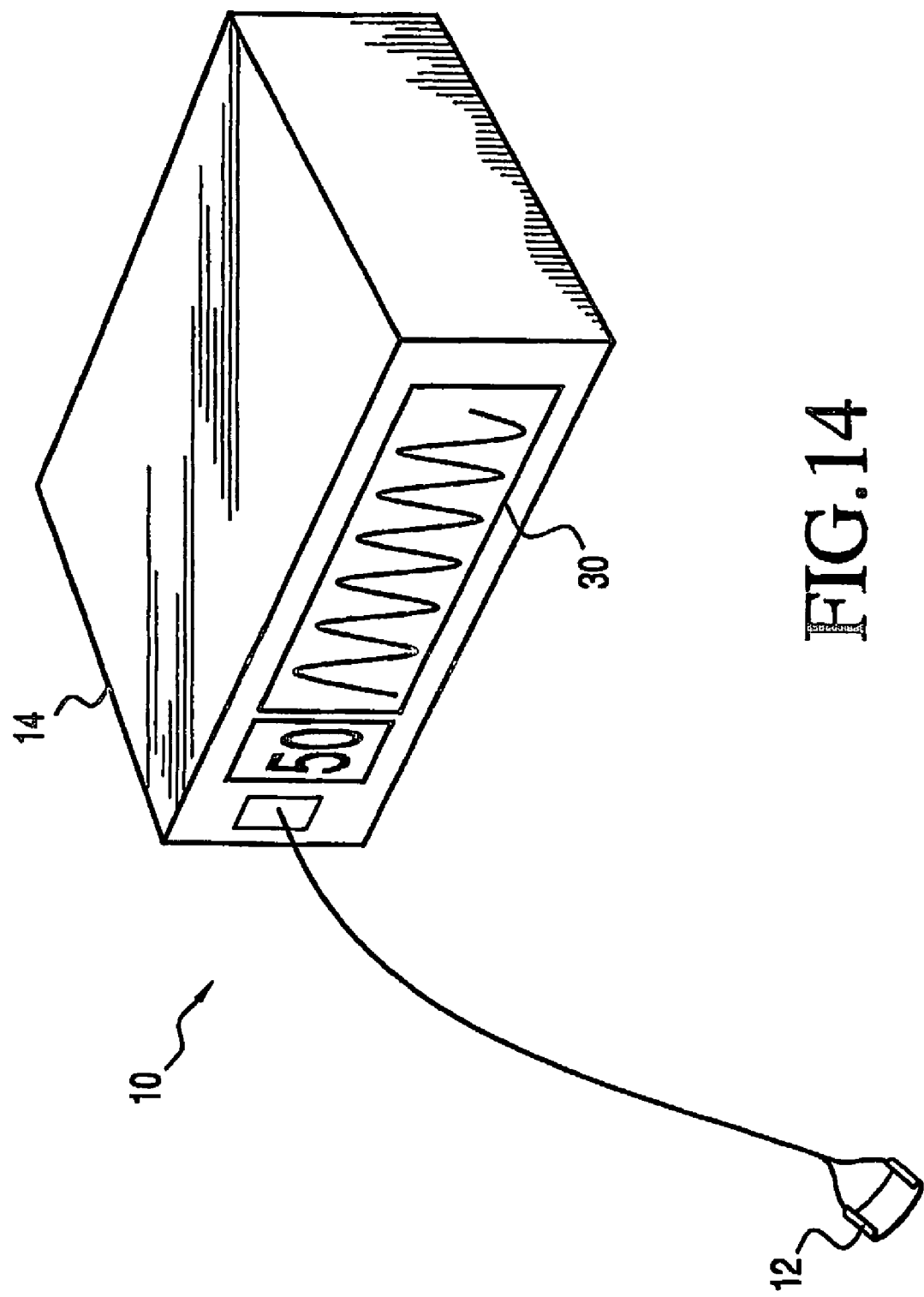
FIG. 14 is a perspective view of a pulse oximeter that may be employed in accordance with the present invention.
Figure 15:
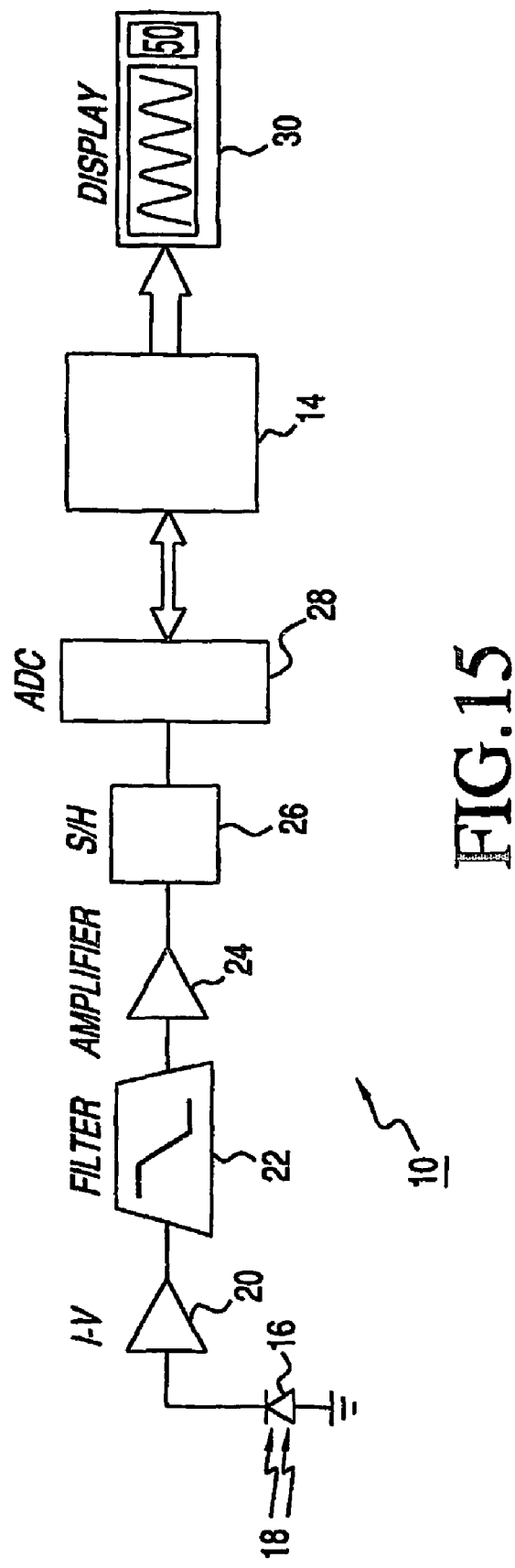
FIG. 15 is a schematic of convention circuitry utilized in conjunction with pulse oximeters.

The present invention is adapted for use with a variety of traditional pulse oximeters, whether employing disposable probes or reusable probes, as well as other related ventilation measuring devices. With reference to FIGS. 14 and 15, an example of a pulse oximeter that may be utilized in accordance with the present invention is disclosed.

Referring to FIGS. 14 and 15, a pulse oximeter 10 is generally composed of a probe 12 adapted for positioning over a patient's finger (or at an alternative site such as the forehead or ear) and a central processor 14 with a display 30 coupled to the probe 12 for receiving and displaying information retrieved by the probe 12. With regard to underlying electrical circuitry, and as described in U.S. Pat. No. 6,496,711, the circuitry for a generic pulse oximeter 10 is disclosed. The pulse oximeter 10 has a photodiode 16 for detecting an optical signal 18 reflected from or transmitted through a volume of intravascular blood (not shown) illuminated by one or more light emitting diodes (LEDs, not shown). The LEDs emit electromagnetic radiation at a constant intensity, however, an optical signal 18 with a time-varying intensity is transmitted through or reflected back from the intravascular blood for each of the wavelengths. The photodiode 16 generates a low-level current proportional to the intensity of the electromagnetic radiation received by the photodiode 16. The current is converted to a voltage by a current to voltage converter 20, which may be an operational amplifier in a current to voltage (transimpedance) configuration.

The signal is then filtered with a filter stage 22 to remove unwanted frequency components, such as any 60 Hz noise generated by fluorescent lighting. The filtered signal is then amplified with an amplifier 24 and the amplified signal is sampled and held by a sample and hold 26 while the signal is digitized with a high-resolution (12-bit or higher) analog to digital converter (ADC) 28.

The digitized signal is then latched by the central processor 14 from the ADC 28. The central processor 14 then calculates a coefficient for the oxygen saturation value from the digitized signal and determines the final saturation value by reading the saturation value for the calculated coefficient from a look-up table stored in memory. The final saturation value is displayed on a display 30.

The methods and systems employed in accordance with the present invention are equally applicable to both mechanically ventilated individuals and spontaneously ventilating individuals. As such, the concepts underlying the present invention equally apply to mechanically ventilated subject under positive pressure, spontaneously ventilating subjects, spontaneously ventilating subjects with positive expiratory pressure and spontaneous ventilating subjects with inspiratory pressure.

However, it is contemplated the waveforms produced by those subjects that are mechanically ventilated exhibit more pronounced variations then those produced by subjects that are spontaneously breathing. This distinction is believed to result from the effect the positive pressure of mechanical ventilation has upon blood pressure and blood flow within a subject. As such, it may be advantageous when monitoring spontaneously ventilating subjects to increase the positive pressure associated with breathing such that the waveforms associated therewith exhibit relevant variations with the same clarity found in mechanically ventilated subjects.

More specifically, while in most cases clinicians and investigators monitoring ventilation simply are interested in the rate and/or depth of respiration, the intrathoracic pressure generated by ventilatory effort is of greater importance when one is assessing the effects of ventilation on peripheral blood flow in accordance with the present invention. This effect, which occurs in synchrony with positive pressure ventilation due to a mechanical ventilator, is termed the "ventilator effect". The periodic oscillations in ventilatory pressure cause synchronous oscillations in continuous waveforms of peripheral blood pressure and peripheral blood flow. Specifically, the periodic delivery of positive pressure by the ventilator impedes the return of blood to the heart and hence causes a transient decrease in the arterial pressure and peripheral flow that may be measured by a device such as a plethysmograph or laser Doppler flow meter.

The degree of oscillatory dampening is determined by: a) the amount of positive pressure that is generated by the ventilator; and b) the patient's relative volume status. The former is commonly measured by the means of positive pressure mechanical ventilation in an intubated patient but, prior to the present disclosure, was not readily attainable during spontaneous (non-mechanical) ventilation, as would be the case in a nonintubated patient. The latter is dependent on the overall fullness of the patient's heart and blood vessels ("volume status"), volume generated with each heartbeat (stroke volume), and the vascular tone. These factors interact such that when a patient is vasodilated or relatively hypovolemic, there is a greater effect of ventilation on peripheral blood pressure and flow.

Figure 16:
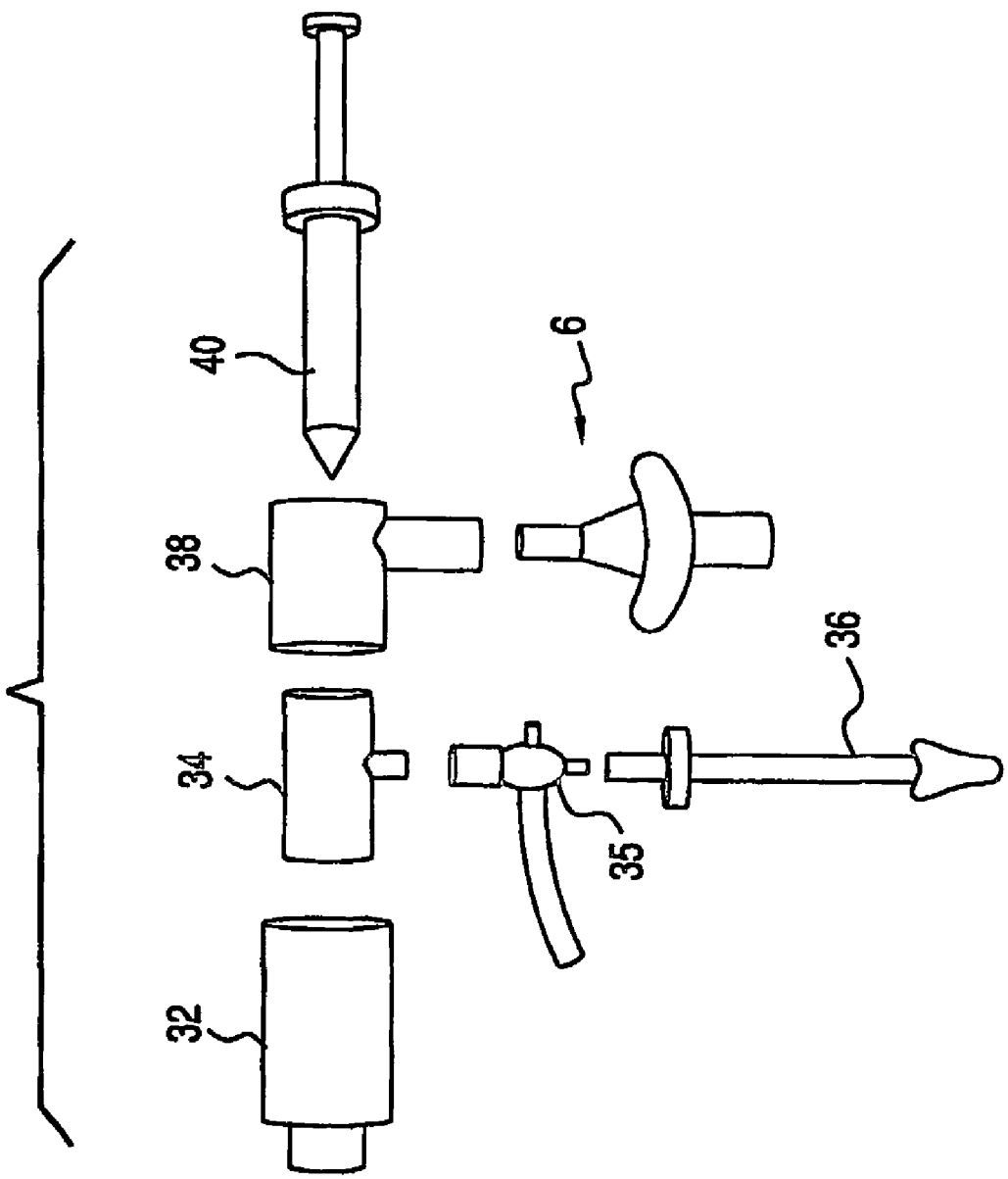
FIG. 16 is an exploded schematic of a positive pressure device in accordance with the present invention.

With reference to FIG. 16, the present positive pressure device has been developed for spontaneously breathing subjects. The device is designed to measure the pressure associated with each breath of ventilation, measure the pressure generated by a prolonged inhalation or exhalation (e.g., Valsalva maneuver), and provide an adjustable resistance so as to enable us to increase or decrease airway pressure in the spontaneously breathing, nonintubated patient, whether that patient be breathing totally on his/he own, or breathing spontaneously in response to a prompt such as a metronome tone.

The device includes a one-way valve 32 and, a connector with side 34 attached via a stopcock 35 to an electronic pressure transducer 36 and/or an anaeroid meter (not shown) for recording and viewing pressure. The device further includes an adaptor 38 for attaching a syringe 40 with occludable holes to provide variable expiratory resistance and a breathing filter 42 through which a subject breathes while holding it in his/her mouth.

The aforementioned system for delivering positive pressure may be packaged separately or integrated with monitors of oscillatory cardiovascular signals (e.g., pulse oximeter). This would enable monitoring of the rate, depth, and pressure of ventilation. The integrated device also could contain a means to prompt a spontaneously breathing patient to breathe at a fixed rate, e.g., a metronome; this would be critical so that one could then determine if the oscillations in the waveform are associated with the ventilatory signal. Additionally, it may be incorporated with a means to monitor rate and depth of respiration by measuring chest and/or abdominal excursion.

In addition to adding positive pressure to those subjects spontaneously ventilating, it has been found that the constant breathing rate of mechanically ventilating subjects produces better waveforms for the purposes of the present invention since the natural variations associated with spontaneous breathing add an additional variable to the process of analyzing the waveforms to determine blood loss. As such, it is contemplated that it may be desirable to associate a spontaneously ventilating subjects breathing rate with a metronome. The breathing rate may also be controlled through the squeezing of a ventilation bag. This will produce a more consistent breathing rate, resulting in more easily analyzed waveforms.

It is further contemplated that the waveforms generated in accordance with the present invention may be analyzed with reference to the pulse wave amplitude, (i.e. normalized) respiratory oscillations, etc. so as to normalize the resulting waveforms in an effort to produce more consistent results from subject to subject and monitoring device to monitoring device.

It is still further contemplated ventilation induced changes in a cardiovascular waveform may be monitored in the context of an irregular rate of respiration. The process includes identifying each respiration and then determining the maximum and minimum of the cardiovascular signal for each respiratory interval.

Especially in the context of spontaneous ventilation with varied intervals between breaths, one may use a respiratory channel as the timing channel for assessment of cardiovascular waveforms. For example, for each breath-to-breath interval, one could record the following from the pulse oximeter signal:

overall mean
peak value for signal within the given breath-to-breath interval
trough value for signal within the given breath-to-breath interval
peak minus trough value for signal within the given breath-to-breath interval min for each heart beat (diastole of given pulse) within the given breath-to-breath interval max for each heart beat (systole of given pulse) within the given breath-to-breath interval max minus min for each heart (amplitude of given pulse) within the given breath-to-breath interval This could be performed for a single breath or for multiple breaths so as to enable assessment of an extended interval such as was used for the aforementioned Fourier transformation.

Using the data illustrated in FIGS. 2a-2c, we obtain the following approximate values for the approximately 8 breaths obtained in a 50 second interval (2000 points/82 points/sec).

| Parameter Being Averaged Over 50-sec Interval | Baseline | 500 cc EBL | 1500 cc EBL |
|---|---|---|---|
| 50-sec Average for Individual Pulses: | | | |
| Systole of pulses | 2.0 | 2.0 | 2.35 |
| Diastole of pulses | −2.0 | −2.2 | −2.3 |
| Amplitude of pulses | 4.0 | 4.2 | 4.65 |
| 50-sec Average for Per-Breath Values: | | | |
| Peak per-breath values of entire waveform | 2.1 | 2.7 | 3.0 |
| Trough per-breath values of entire waveform | −1.85 | −2.55 | −3.2 |
| Difference between peak and trough per-breath values of entire waveform | 3.95 | 5.25 | 6.2 |
| Peak per-breath values of arterial portion of waveform | 2.1 | 2.7 | 3.0 |
| Trough per-breath values of arterial portion of waveform | 2.0 | 2.1 | 1.8 |
| Difference between peak and tough per-breath values of arterial portion of waveform | 4.1 | 4.8 | 5.8 |
| Peak per-breath values of venous portion of waveform | −1.95 | −2.15 | −2.15 |
| Trough per-breath values of venous portion of waveform | −2.1 | −2.55 | −3.0 |
| Difference between peak and tough per-breath values of venous portion of waveform | 4.05 | 4.70 | 5.15 |
| Largest per-breath pulse amplitude | 4.0 | 4.5 | 5.0 |
| Smallest per-breath pulse amplitude | 3.8 | 3.8 | 4.0 |
| Difference between Largest per-breath and smallest per-breath pulse amplitudes | 0.2 | 0.7 | 1.0 |
| Highest per-breath height of dicrotic notch | −0.8 | −1.3 | −1.0 |
| Lowest per-breath height of dicrotic notch | −1.3 | −2.2 | −2.2 |
| Difference between highest per-breath and lowest per-breath heights of dicrotic notch | 0.5 | 0.9 | 1.2 |

It should be noted that, in addition to assessment of power at different frequencies the phase angle between the different measurements (e.g., graphic delineation of local mins vs local maxs) and changes in the different measurements may be determined as per published work described in Podgoreanu M V, Stout R G, El-Moalem E, Silverman D G, *Synchronous rhythmical vasomotion in the human cuatneous microvasculature during nonpulsatile cardiopulmonary bypass*, Anesthesiology 2002; 97:1110-1116, which adapted the technique for determining phase angle described by Bernardi L, et al., *Synchronous and baroreceptor-sensitive oscillators in skin microcirculation: evidence for central autonomic control*, Am J Physiol 1997; 273: H1867-1878.

The aforementioned means to identify and segregate the arterial and venous components of a cardiovascular waveform such as the plethysmographic waveform of a pulse oximeter, enable one to selectively monitor the arterial or venous component of that waveform with respect to flow (or pressure). They also enable one to select the time of the determination of a measurement such as oxygen saturation so as to isolate arterial oxygenation from venous oxygenation.

In addition, the delineation of the arterial and venous components enables one to modify the actual plethysmographic tracing by a means such as application of pressure to the monitoring probe to a degree that obliterates the low pressure (venous or DC) component. This would cause the tracing to more closely resemble the arterial tracing generated by an intra-arterial catheter. This sequence of steps is illustrated in FIGS. 17 and 18.

It should further be appreciated that the methods of the present invention may include the additional step of monitoring the rate of respiration. This may further include integrating the respiratory signal into a data collection system which also collects input from a cardiovascular signal, identifying one or more breath-to-breath intervals, using the breath-to-breath intervals as the "timing channel" for assessment of the cardiovascular waveform and determining the magnitude and change of the cardiovascular waveform for the given breath or breaths.

The indices which may be measured in accordance with the present invention are systole, diastole, and/or amplitude of one or more individual pulses. More specifically, the indices monitored include one or more of the following indices determined for one or more intervals: peak per-breath values of entire waveform, trough per-breath values of entire waveform, difference between peak and trough per-breath values of entire waveform, peak per-breath values of arterial portion of waveform; trough per-breath values of arterial portion of waveform; difference between peak and tough per-breath values of arterial portion of waveform; peak per-breath values of venous portion of waveform, trough per-breath values of venous portion of waveform, difference between peak and tough per-breath values of venous portion of waveform, largest per-breath pulse amplitude, smallest per-breath pulse amplitude, difference between largest per-breath and smallest per-breath pulse amplitudes, highest per-breath height of dicrotic notch, lowest per-breath height of dicrotic notch, and difference between highest per-breath and lowest per-breath heights of dicrotic notch.

The method and system of the present invention may also be utilized where there is positive inspiratory and/or expiratory pressure during ventilation, and wherein the amount of positive pressure is quantified and adjustable. The method and system may also provide that the change in the cardiovascular monitor attributed to respiration is normalized to (e.g., expressed as a percentage of) the inspiratory or expiratory pressure and the variation in the cardiovascular monitor attributed to ventilation is normalized to the amplitude of the individual pulse beats.

In addition, the present method and system may also provide that outputs of different monitoring devices obtained from one or more monitoring sites are compared. In this instance the devices may both be pulse oximeters, or one or more of the devices may be an alternative continuous measure of blood flow (e.g., laser Doppler flow meter) or a continuous measure of blood pressure.

In practicing the present method and system it is contemplated that pressure may be applied to a monitoring device such as an oximeter probe to eliminate the venous component of the tracing and the pressure to eliminate the venous component is quantified so that the venous pressure may be measured. In addition, the present method and system provides that oxygen saturation may be determined independently for the arterial and venous phases.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A method for assessing changes in blood volume within a subject, the method comprising:
   generating a cardiovascular waveform representing physiological characteristics of a subject;
   detecting changes in blood volume of the subject by analyzing the cardiovascular waveform using a processor, wherein the analyzing of the cardiovascular waveform includes:
      applying harmonic analysis to the cardiovascular waveform;
      extracting a signal created by ventilation; and
      analyzing changes in signal strength of the extracted signal to detect changes in blood volume of the subject.

2. The method according to claim 1, wherein the cardiovascular waveform is a photoplethysmograph waveform.

3. The method according to claim 1, wherein the harmonic analysis includes Fourier analysis.

4. The method according to claim 1, wherein the harmonic analysis includes joint time-frequency analysis.

5. The method according to claim 1, wherein the harmonic analysis includes a short-time Fourier transformation.

6. The method according to claim 1, wherein the extraction of the signal is achieved using a peak detection algorithm.

7. The method according to claim 6, wherein the peak detection algorithm is applied in the frequency range of ventilation.

8. The method according to claim 1, wherein the cardiovascular waveform is generated using a photoplethysmographic device.

9. The method according to claim 1, wherein one or more oscillations of the cardiovascular waveform are representative of ventilatory related fluctuation.

10. The method according to claim 1, wherein the determining the changes in blood volume includes monitoring a signal in a respiratory frequency range to ascertain changes in a venous component of blood volume.

11. The method according to claim 1, wherein the determining the changes in blood volume includes monitoring side bands surrounding a signal in a cardiac frequency range to ascertain changes in the arterial component of the blood volume.

12. The method according to claim 1, wherein ventilation of the subject is synchronized with a metronome.

13. A method for facilitating detection of physiological changes of a subject, the method comprising:
   analyzing a cardiovascular waveform representing physiological characteristics of a subject using a processor, wherein the analyzing of the cardiovascular waveform includes:
      identifying a first component of the cardiovascular waveform reflective of a cardiovascular impact of respiration; and
      analyzing a characteristic of the first component reflective of amplitude variations of the first component, wherein the amplitude variations are indicative of changes in blood volume of the subject.

14. The method of claim 13, wherein the first component of the cardiovascular waveform is a systolic component reflective of a cardiovascular impact of respiration on per cardiac-cycle maximums of the cardiovascular waveform.

15. The method of claim 13, wherein the first component of the cardiovascular waveform is a diastolic component reflective of a cardiovascular impact of respiration on per cardiac-cycle minimums of the cardiovascular waveform.

16. The method of claim 13, wherein the first component of the cardiovascular waveform is reflective of a cardiovascular impact of respiration on per heart-beat dicrotic notches of the cardiovascular waveform.

17. The method of claim 13, wherein the first component of the cardiovascular waveform is an arterial component reflective of a cardiovascular impact of respiration on an amplitude of a cardiac-signal component of the cardiovascular waveform, wherein the amplitude variations of the arterial component are indicative of changes in arterial blood volume of the subject.

18. The method of claim 13, wherein the first component of the cardiovascular waveform is a venous component reflective of a cardiovascular impact of respiration on a baseline of a cardiac-signal component of the cardiovascular waveform, wherein the amplitude variations of the venous component are indicative of changes in venous blood volume of the subject.

19. The method of claim 13, wherein the cardiovascular waveform is analyzed in at least one of (i) the time domain, (ii) the frequency domain and (iii) the joint time-frequency domain.

20. The method of claim 13, wherein the analyzed characteristic is reflective of at least one of (i) changes in per respiratory-cycle maximums of the first component in the time domain, (ii) changes in per respiratory-cycle minimums of the first component in the time domain, and (iii) changes in a difference between corresponding per respiratory-cycle maximums and per respiratory-cycle minimums of the first component in the time domain; and (iv) changes in a signal strength of the first component in the frequency domain.

21. The method of claim 13, wherein the cardiovascular waveform is analyzed using harmonic analysis to identify the first component of the cardiovascular waveform.

22. The method of claim 21, wherein the identifying the first component of the cardiovascular waveform is achieved using a peak detection algorithm on the cardiovascular waveform applied in the frequency domain.

23. The method of claim 21, wherein the first component of the cardiovascular waveform is an arterial component reflective of a cardiovascular impact of respiration on an amplitude of a cardiac-signal component of the cardiovascular waveform, wherein the amplitude variations of the arterial component are identified based on side bands surrounding a primary cardiac signal component in the cardiac frequency range, and wherein the amplitude variations of the arterial component are indicative of changes in arterial blood volume of the subject.

24. The method of claim 21, wherein the first component of the cardiovascular waveform is a venous component reflective of a cardiovascular impact of respiration on a baseline of a cardiac-signal component of the cardiovascular waveform, wherein the venous component is identified in the respiratory frequency range, and wherein the amplitude variations of the venous component are indicative of changes in venous blood volume of the subject.

25. The method of claim 13, wherein the first component is normalized based on an amplitude of a cardiac signal component of the cardiovascular waveform.

26. The method of claim 13, wherein the analyzing the characteristic of the first component of the cardiovascular waveform includes calculating an index responsive to the amplitude variations of the first component, wherein index variations are indicative of physiological changes in the subject.

27. The method of claim 13, further comprising monitoring fluid responsiveness of the subject based on the analysis of the characteristic of the first component.

28. The method of claim 13, further comprising detecting hypovolemia based on the analysis of the characteristic of the first component.

29. The method of claim 13, further comprising detecting dehydration based on the analysis of the characteristic of the first component.

30. The method of claim 13, wherein subject respiration is synchronized with a metronome.

31. The method of claim 13, wherein airway pressure is at least one of (i) actively controlled and (ii) standardized.

32. The method of claim 13, wherein the first component is normalized based on one of (i) respiratory oscillations and (ii) airway pressure.

33. A system for assessing changes in blood volume within a subject, the system comprising:
a probe adapted for generating a cardiovascular waveform of a subject; and
a processor configured for analyzing the cardiovascular waveform to determine changes in blood volume of the subject, wherein the analyzing of the cardiovascular waveform includes:
applying harmonic analysis to the cardiovascular waveform;
extracting a signal created by ventilation; and
applying the extracted signal in determining the changes in blood volume of the subject, wherein the applying the extracted signal includes monitoring changes in a signal strength of the extracted signal in the frequency domain.

34. The system according to claim 33, wherein the probe is photoplethysmographic device and the cardiovascular waveform is a photoplethysmograph waveform.

35. The system according to claim 33, wherein the harmonic analysis includes Fourier analysis.

36. The system according to claim 33, wherein the harmonic analysis includes joint time-frequency analysis.

37. The system according to claim 36, wherein the harmonic analysis includes a short-time Fourier transformation.

38. The system according to claim 33, wherein the extraction of the signal is achieved using a peak detection algorithm.

39. The system according to claim 38, wherein the peak detection algorithm is applied in the frequency range of ventilation.

40. The system according to claim 33, wherein the determining the changes in blood volume includes monitoring a signal in a respiratory frequency range to ascertain changes in a venous component of blood volume.

41. The system according to claim 33, wherein the determining the changes in blood volume includes monitoring side bands surrounding a signal in a cardiac frequency range to ascertain changes in the arterial component of the blood volume.

42. The system according to claim 33, wherein ventilation of the subject is synchronized with a metronome.

43. A system for facilitating detection of physiological changes of a subject, the system comprising:
a probe adapted for generating a cardiovascular waveform representing physiological characteristics of a subject; and
a processor configured for analyzing the cardiovascular waveform, wherein the analyzing the cardiovascular waveform includes identifying a first component of the cardiovascular waveform reflective of a cardiovascular impact of respiration, and analyzing a characteristic of the first component reflective of amplitude variations of the first component, wherein the amplitude variations are indicative of changes in blood volume of the subject.

44. The system of claim 43, wherein the first component of the cardiovascular waveform is a systolic component reflective of a cardiovascular impact of respiration on per cardiac-cycle maximums of the cardiovascular waveform.

45. The system of claim 43, wherein the first component of the cardiovascular waveform is a diastolic component reflective of a cardiovascular impact of respiration on per cardiac-cycle minimums of the cardiovascular waveform.

46. The system of claim 43, wherein the first component of the cardiovascular waveform is reflective of a cardiovascular impact of respiration on per heart-beat dicrotic notches of the cardiovascular waveform.

47. The system of claim 43, wherein the first component of the cardiovascular waveform is an arterial component reflective of a cardiovascular impact of respiration on an amplitude of a cardiac-signal component of the cardiovascular waveform, wherein the amplitude variations of the arterial component are indicative of changes in arterial blood volume of the subject.

48. The system of claim 43, wherein the first component of the cardiovascular waveform is a venous component reflective of a cardiovascular impact of respiration on a baseline of a cardiac-signal component of the cardiovascular waveform, wherein the amplitude variations of the venous component are indicative of changes in venous blood volume of the subject.

49. The system of claim 43, wherein the cardiovascular waveform is analyzed in at least one of (i) the time domain, (ii) the frequency domain and (iii) the joint time-frequency domain.

50. The system of claim 43, wherein the analyzed characteristic is reflective of at least one of (i) changes in per respiratory-cycle maximums of the first component in the time domain, (ii) changes in per respiratory-cycle minimums of the first component in the time domain, and (iii) changes in a difference between corresponding per respiratory-cycle maximums and per respiratory-cycle minimums of the first component in the time domain; and (iv) changes in a signal strength of the first component in the frequency domain.

51. The system of claim 43, wherein the cardiovascular waveform is analyzed using harmonic analysis to identify the first component of the cardiovascular waveform.

52. The system of claim 51, wherein the identifying the first component of the cardiovascular waveform is achieved using a peak detection algorithm on the cardiovascular waveform applied in the frequency domain.

53. The system of claim 51, wherein the first component of the cardiovascular waveform is an arterial component reflective of a cardiovascular impact of respiration on an amplitude of a cardiac-signal component of the cardiovascular waveform, wherein the amplitude variations of the arterial component are identified based on side bands surrounding a primary cardiac signal component in the cardiac frequency range, and wherein the amplitude variations of the arterial component are indicative of changes in arterial blood volume of the subject.

54. The system of claim 51, wherein the first component of the cardiovascular waveform is a venous component reflective of a cardiovascular impact of respiration on a baseline of a cardiac-signal component of the cardiovascular waveform, wherein the venous component is identified in the respiratory frequency range, and wherein the amplitude variations of the venous component are indicative of changes in venous blood volume of the subject.

55. The system of claim 43, wherein the first component is normalized based on an amplitude of a cardiac signal component of the cardiovascular waveform.

56. The system of claim 43, wherein the analyzing the characteristic of the first component of the cardiovascular waveform includes calculating an index responsive to the amplitude variations of the first component, wherein index variations are indicative of physiological changes in the subject.

57. The system of claim 43, wherein the analyzing the cardiovascular waveform further includes monitoring fluid responsiveness of the subject based on the analysis of the characteristic of the first component.

58. The system of claim 43, wherein the analyzing the cardiovascular waveform further includes detecting hypovolemia based on the analysis of the characteristic of the first component.

59. The system of claim 43, wherein the analyzing the cardiovascular waveform further includes detecting dehydration based on the analysis of the characteristic of the first component.

60. The system of claim 43, further comprising a metronome adapted for synchronizing subject respiration.

61. The system of claim 43, further comprising an airway pressure control adapted for at least one of (i) actively controlling airway pressure and (ii) standardizing airway pressure.

62. The system of claim 43, wherein the first component is normalized based on one of (i) respiratory oscillations and (ii) airway pressure.

* * * * *